US006531134B1

(12) United States Patent
Dunbar et al.

(10) Patent No.: US 6,531,134 B1
(45) Date of Patent: Mar. 11, 2003

(54) MAMMALIAN MILK GROWTH FACTOR

(75) Inventors: Andrew Jeremy Dunbar, Adelaide (AU); Christopher Goddard, Blackwood (AU); David Andrew Belford, Seacliff (AU)

(73) Assignee: Gropep Pty Ltd., South Australia (AU)

( * ) Notice: Subject to any disclaimer, the term of this patent is extended or adjusted under 35 U.S.C. 154(b) by 0 days.

(21) Appl. No.: 09/554,119

(22) PCT Filed: Nov. 12, 1998

(86) PCT No.: PCT/AU98/00942

§ 371 (c)(1),
(2), (4) Date: May 10, 2000

(87) PCT Pub. No.: WO99/24470

PCT Pub. Date: May 20, 1999

(30) Foreign Application Priority Data

Nov. 12, 1997 (AU) .............................................. PP-0318

(51) Int. Cl.[7] ........................ A61K 39/00; A61K 38/00; C07K 14/00; C07K 17/00; C12P 21/06
(52) U.S. Cl. ........................ 424/198.1; 514/2; 530/350; 530/399; 435/69.1
(58) Field of Search ................................. 530/350, 399; 514/2; 435/69.1; 424/198.1

(56) References Cited

U.S. PATENT DOCUMENTS

| 5,328,986 A | 7/1994 | Folkman et al. |
| 5,461,033 A | * 10/1995 | Donnet et al. ................. 514/12 |

FOREIGN PATENT DOCUMENTS

| EP | 0555785 A1 | 8/1993 |

OTHER PUBLICATIONS

Scopes, Biotech. Appl. Biochem., 1996, vol. 23, 197–204.*

* cited by examiner

*Primary Examiner*—Yvonne Eyler
*Assistant Examiner*—Janet L. Andres
(74) *Attorney, Agent, or Firm*—Birch, Stewart, Kolasch & Birch, LLP

(57) ABSTRACT

A mammalian milk growth factor (MMGF) having the following amino acid sequence or substantially homologous sequence: DGNSTRSPEDDGLLCGDHAENC-PATTTQPKRRGHFSRCPKQYKHYCIKGR-CRFVVAEQTPSCVCDEGYAGARCERVDLFY (SEQ ID NO:2) or a mutant, analogue, derivative or functionally active fragment thereof.

24 Claims, 13 Drawing Sheets

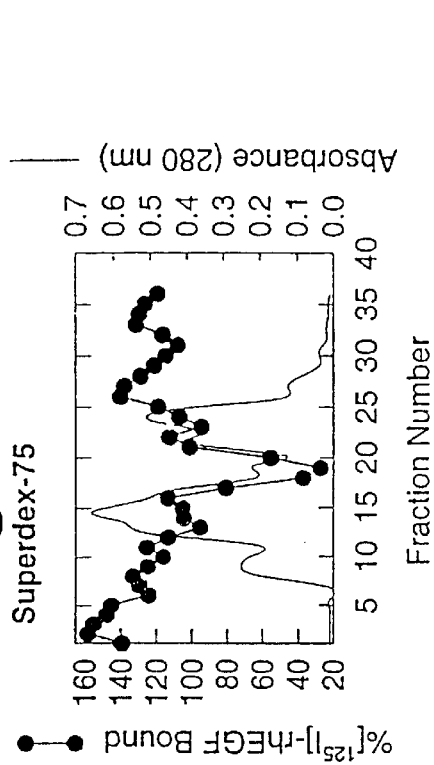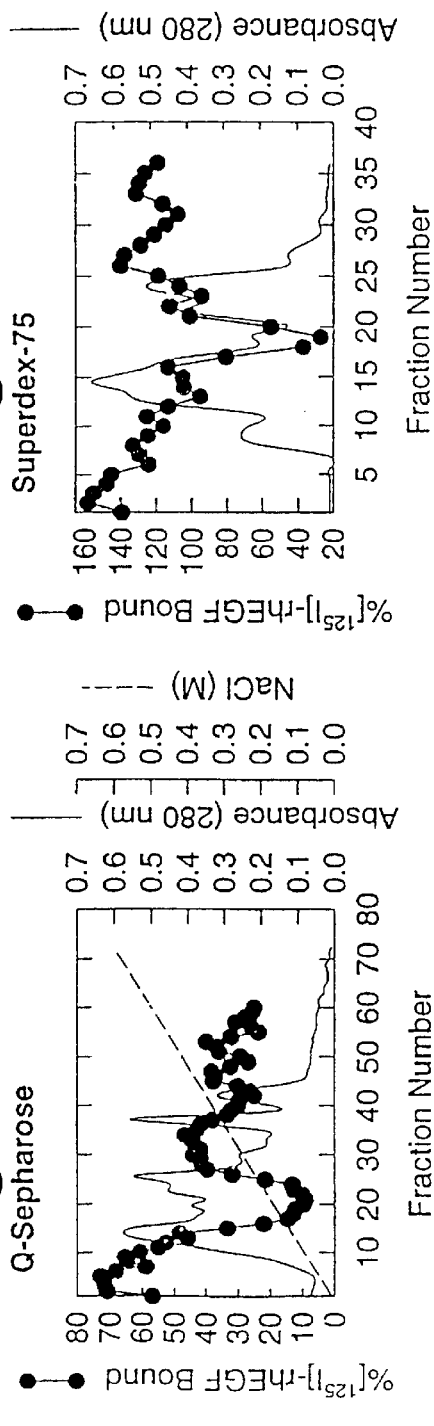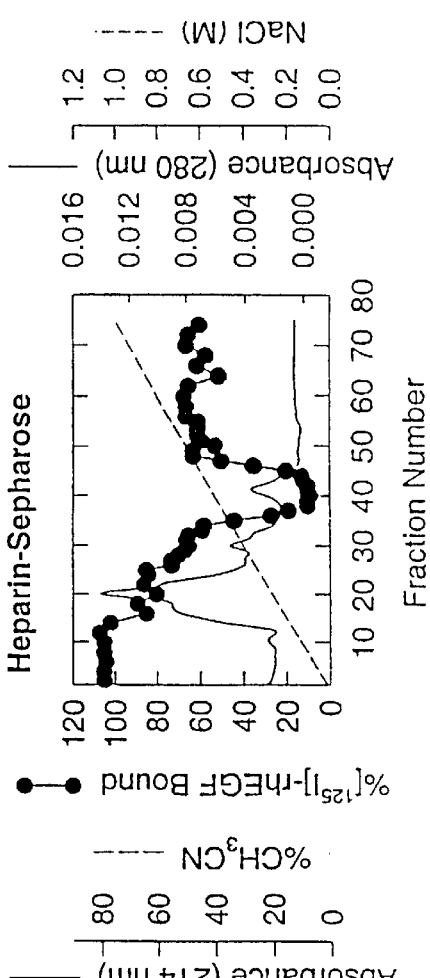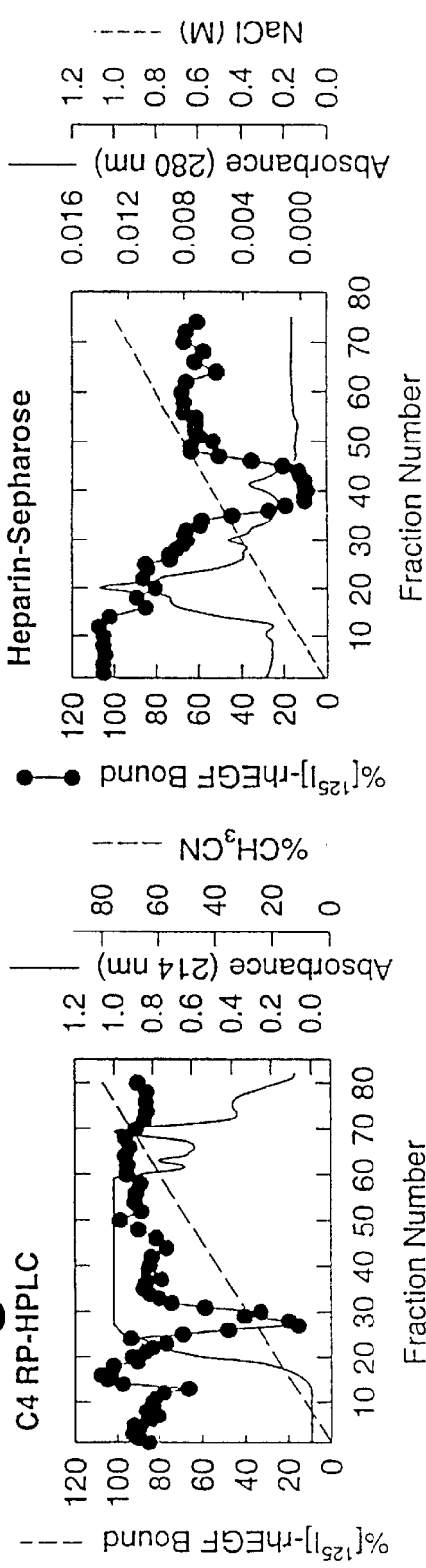

Figure 3

Deduced Sequence:

```
         10        20        30        40        50        60        70        80
DGNSTRSPEDDGLLCGDHAENCPATTQPKRRGHFSRCPKQYKHYCIKGRCRFVVAEQTPSCVVCDEGYAGARCERVDLFY
```

N-terminal sequence:

```
DCXSXRSPEDDGLLCGDHAENCPATTQPKRRGHF
```

Endoproteinase Lys-C peptides:

```
DCXSXRSPEDDGLLCGDHAENCPATTQPK
                             RRGHFSRCPK
                                       QYK
                                          HYCIK
                                               GRCRFVVAEQTPSCVVCDEGYAGARCERVDLFY
```

Figure 5

```
  1   D   G   N   S   T   R   S   P   E   D   D   G   L   L   C    15
  1  GAT GGG AAT TCA ACC AGA AGT CCT GAA GAT GAT GGC CTT CTT TGT   45

16   G   D   H   A   E   N   C   P   A   T   T   Q   P   K    30
 46  GGA GAT CAC GCA GAA AAC TGC CCA GCT ACC ACA CAA CCA AAG   90

31   R   R   G   H   F   S   R   C   P   K   Q   Y   K   H   Y    45
 91  CGA AGA GGC CAC TTC TCT CGG TGC CCC AAG CAG TAC AAG CAT TAC  135

46   C   I   K   G   R   C   R   F   V   V   A   E   Q   T   P    60
136  TGC ATT AAA GGG AGA TGT CGC TTC GTG GTG GCC GAG CAG ACG CCC  180

61   S   C   V   C   D   E   G   Y   A   G   A   R   C   E   R    75
181  TCC TGC GTC TGT GAT GAA GGC TAT GCT GGG GCC AGA TGT GAG AGA  225

76   V   D   L   F   Y    80
226  GTT GAC TTG TTT TAC  240
```

Balb/c 3T3

Balb/c 3T3

IEC-6

HaCat

SF3169

CalOst

MAMMALIAN MILK GROWTH FACTOR

This application is the national phase under 35 U.S.C. §371 of PCT International Application No. PCT/AU98/00942 which has ah International filing date of Nov. 12, 1998, which designated the United States of America.

The present invention relates to a novel growth factor from bovine milk, milk products or milk product extracts. The present invention also relates to the use of recombinant DNA technology to isolate, clone and sequence nucleic acids encoding the mature and precursor forms of the growth factor and, in addition, to the use of these nucleic acids in the recombinant production of the growth factor.

Growth factors are implicated in a wide range of physiological and pathological processes such as cell communication, growth and development, apoptosis, embryogenesis, initiation of the immune response, cell survival and differentiation, wound healing, and cancer. Justifiably, there is a great deal of interest in isolating, characterising and defining the functional mechanisms of growth factors, not only in understanding the basic mechanisms behind normal growth control, but also because of their potential therapeutic use.

Growth factors may also comprise an essential component of defined media used in the growth of cells in culture by the biotechnology industry. For many years animal sera have been used to supplement culture media to provide essential components for cell growth. Foetal bovine serum (FBS) is most commonly used, however there are market and regulatory concerns about the safety of animal and human sourced proteins in pharmaceutical manufacturing processes.

Despite the considerable progress made using milk based alternatives to serum, the safety concerns surrounding mammalian body fluids as supplements for cell culture media (as a consequence of the potential for infection with latent pathogens (eg. bovine spongiform encephalopathy (BSE)) means that these are considered unsafe. Therefore attention has focussed on the development of completely defined cell culture media containing growth factors of known origin and defined purity. This means that the growth factor component of cell culture media is provided by purified native or recombinant molecules.

Milk is an important nutrient required for the growth and development of an infant. It is a source of nutrients such as casein, lactoferrin, lactalbumin, lactose and various other compounds such as vitamins, ions, enzymes etc. A number of growth factors have been identified in human and bovine milk. These include Insulin-like growth factor I and II, fibroblast growth factors, transforming growth factor β, and platelet-derived growth factor. Although epidermal growth factor is present in human milk it has not been convincingly demonstrated in bovine milk (Iacopetta et al, Acta Paediatr, 81, 287, (1992)). Several roles have been proposed for milk-derived growth factors including development and differentiation of the mammary gland (Collier et al, Livestock Production Science, 35, 21, (1993)), regulation of the developing neonatal immune system (Ishizaka et al. Cellular Immunol, 159, 77, (1994)), gastrointestinal growth and maturation (Read et al, Pediatric Research, 18, 133, (1984)), and possible actions in other organs. Milk-derived growth factors have also been shown to support the growth of a variety of cells in culture. In addition, bovine milk whey, the by-product of cheese manufacture, can also support the growth of mammalian cells in the short or long term (Derouiche et al, Lait, 70, 313, (1990); Damerdji et al, Biotechnology Tech, 2, 253, (1988)) and has been shown to possess antitumor activity (Bounous et al, Clin. Invest. Med. 11, 312, (1988)). The prior art also includes Australian patent 645589 to the present applicant which describes the use of a bovine milk whey extract, containing a plurality of cell growth stimulating factors, as a replacement for serum in mammalian cell culture.

It is an object of the present invention to overcome, or at least alleviate, one or more of the difficulties or deficiencies associated with the prior art. Accordingly, in a first aspect of the present invention there is provided a novel growth factor, hereinafter referred to as Bovine Milk Growth Factor (BMGF) obtainable from bovine milk, milk products or milk product extracts. The term "milk" as used herein refers to lactational secretions of human or animal origin.

The BMGF may be in a substantially pure or partially pure form. The term "substantially pure" as used herein to describe the purity of BMGF means at least 70% pure.

The term "partially pure" as used herein to describe the purity of BMGF means a specific activity greater than 0.3 units per milligram protein.

The term "one unit" as used herein as a measure of BMGF activity is defined as the amount of BMGF required to compete for 50% of the binding of $^{125}$I-labelled recombinant human epidermal growth factor to AG2804 cells under the assay conditions described in Example 1 of this specification.

The native BMGF in its glycosylated form may have a molecular weight of approximately 21 to 25 kDa as determined by SDS-PAGE. It has the ability to stimulate the proliferation of fibroblasts and/or epithelial cells.

In a preferred form of this aspect of the invention the BMGF has an amino acid sequence as follows:
DGNSTRSPEDDGLLCGDHAENC-PATTTQPKRRGHFSRCPKQYKHYCIKGR-CRFVVAEQTPSCVCDEGYAGARCERVDLFY (SEQ ID NO:2)

The BMGF disclosed herein may be a member of the epidermal growth factor family of growth factors. It contains eighty amino acid residues and eight half cysteines, a pattern that has also been described for an epidermal growth factor-like molecule purified from the conditioned media of mouse pancreatic beta tumor cells (Shing et al, Science, 259, 1604, (1993)). The amino acid sequence of the human form of this factor, termed, betacellulin, has also been deduced from a nucleotide sequence obtained from a human adenocarcinoma cell line (Sasada et al, Biochem. Biophys. Res. Commun. 190, 1173, (1993)). It is likely, based on the sequence homologies between BMGF and mouse betacellulin (58 identical residues) and with human betacellulin (72 identical residues), that BMGF is the bovine form of the betacellulin. Clearly, it is not the same molecule. The BMGF isolated from bovine cheese whey extract has a molecular mass of 21–25 kDa, which is substantially smaller in size than the 32 kDa reported for the natural mouse betacellulin.

The present invention also includes within its scope precursor forms of BMGF and functionally active fragments (peptides) of BMGF. Such fragments may have enhanced or diminished growth stimulatory activity and/or may expand or limit the range of cells responsive to BMGF's growth stimulatory activity. They may find useful applications in areas such as, but not limited to, the repair or prevention of gut damage or in wound healing.

They may be produced by methods known to those skilled in the art. Procedures at the genetic level such as (but not limited to) site-directed mutagenesis or at the protein level such as (but not limited to) chemical modification are within the scope of the invention.

In a preferred form of this aspect of the invention the fragments of BMGF may include the following amino acid sequences:

DGNSTRSPEDDGLLCGDHAENCPATTTQPKRRGHF (SEQ ID NO:3); or
GYAGARCERVDLFY (SEQ ID NO:4); or
DGNSTRSPEDDGLLCGDHAENCPATTTQPK (SEQ ID NO:5); or
RRGHFSRCPK (SEQ ID NO:6); or
QYK (SEQ ID NO:7); or
HYCIK (SEQ ID NO:8); or
GRCRFVVAEQTPSCVCDEGYAGARCERVDLFY (SEQ ID NO:9)

The present invention also provides BMGF that is substantially non-glycosylated. This may be prepared, for example, by subjecting glycosylated BIZGF to an enzymatic deglycosylation step and recovering the de-glycosylated form. The BMGF in its non-glycosylated or partially non-glycosylated form may have a molecular weight of approximately 9–14 kDa as determined by SDS-PAGE.

In a further preferred form of this aspect of the invention, the BMGF is obtained from bovine milk, bovine milk products or bovine milk product extracts. Moire preferably it is obtained from cheese whey, most preferably from bovine cheese whey extract.

In a further aspect of the present invention, there is provided a process for the isolation, in a substantially pure or partially pure form, of BMGF from bovine milk or milk products. More preferably it is isolated from cheese whey or a cheese whey extract, most preferably from bovine cheese whey or bovine cheese whey extract. The BMGF in its glycosylated form has a molecular weight of approximately 21 to 25 kDa as determined by SDS-PAGE. It may have the ability to stimulate the proliferation of fibroblasts and/or epithelial cells, and/or osteoblast cells.

In a preferred form of this aspect of the invention the BMGF has an amino acid sequence as follows:

DGNSTRSPEDDGLLCGDHAENC-
PATTTQPKRRGHFSRCPKQYKHYCIKGR-
CRFVVAEQTPSCVCDEGYAGARCERVDLFY (SEQ ID NO:2)

The process of isolating substantially pure BMGF in this aspect of the invention may include subjecting the milk or a milk product or milk product extract to various purification steps such as ion-exchange chromatography, size-exclusion chromatography, affinity chromatography and reverse-phase high performance liquid chromatography and/or if necessary further purification processes. A "milk product" may include cheese whey, skim milk, acid (Casein) whey and colostrum. Preferably, the milk or milk product is subjected to a process outlined in AU645589 to provide a milk product extract prior to the purification steps outlined above. The contents of AU645589 are incorporated herein. A "milk product extract" is defined herein as an extract prepared from milk or a milk product by a process described in Australian Patent AU645589. By way of clarification, the defining of a milk product extract encompasses a cheese whey extract.

Sample fractions collected from each purification step, and which show biological activity in a radioreceptor assay using AG2804 cells are pooled and forwarded to the next purification step. Sample material from each of the pooled fractions may be subjected to a dose response analysis, thereby allowing for an estimate of the amount of material required to elicit a 50% response of the maximal activity in the said assay. This said amount, in conjunction with the values for the amount of material in each pool, may be used to calculate the yield of purification recovery, and specific activity at each step of the process. Homogeneity of substantially pure BMGF may be demonstrated by:
migration as a single band of approximately 21–25 kDa following SDS-PAGE,
N-terminal sequence analysis,
mass spectroscopy and/or
specific binding to an EGF-receptor In a preferred form of this aspect of the invention there is provided a method of isolating substantially pure BMGF which method includes
providing bovine milk, milk product or milk product extract;
subjecting the bovine milk, milk product or milk product extract to ultrafiltration to obtain a first fraction;
subjecting the first fraction to anion exchange chromatography to obtain a second fraction;
subjecting the second fraction to gel filtration chromatography to obtain a third fraction;
subjecting the third fraction to reverse phase high performance liquid chromatography ((RP)HPLC) to obtain a fourth fraction;
subjecting the fourth fraction to affinity chromatography to obtain a fifth fraction;
subjecting the fifth fraction to (RP)HPLC to obtain a sixth fraction;
subjecting the sixth fraction to (RP)HPLC to obtain the substantially pure BMGF.

In a further preferred form of this aspect of the invention there is provided a method of isolating substantially pure BMGF which method includes
providing a milk product extract prepared according to AU645589;
subjecting the milk product extract to acidification;
subjecting the acidified milk product extract to ultrafiltration to obtain a first fraction;
subjecting the first fraction to anion exchange chromatography to obtain a second fraction;
subjecting the second fraction to gel filtration chromatography to obtain a third fraction;
subjecting the third fraction to reverse phase high performance liquid chromatography ((RP)HPLC) to obtain a fourth fraction;
subjecting the fourth fraction to affinity chromatography to obtain a fifth fraction;
subjecting the fifth fraction to (RP)HPLC to obtain a sixth fraction;
subjecting the sixth fraction to (RP)HPLC to obtain the substantially pure BMGF.

Preferably, the milk, milk product or milk product extract is subjected to an acidification step. Preferably the acidification is conducted prior to ultrafiltration. More preferably the acidification is conducted at a pH 2.5.

Preferably the ultrafiltration is performed using a membrane with an exclusion limit of approximately 50–150 kDa, more preferably approximately 100 kDa.

Preferably the anion exchange chromatography is performed using an agarose-based anion exchange column.

Preferably the gel filtration is performed using a column which separates proteins having molecular weights in the range approximately 3 kDa to 70 kDa.

Preferably the first: (RP)HPLC is performed using a C4 or C18 matrix.

Preferably the affinity chromatography is performed using a heparin/agarose-based affinity column.

Preferably the second (RP)HPLC is performed using a C4 or C18 matrix.

Preferably the third (RP)HPLC is performed using a C4 or C18 matrix.

As an alternative to producing a milk product extract prepared according to AU645589 as the starting material, a bovine milk or milk product may be utilised. If this approach is adopted a preliminary purification step may be used to remove the fat, solids and acidic proteins before the anion exchange chromatography step.

The substantially purified BMGF may be used in the production of polyclonal and monoclonal antibodies which recognise and/or bind to BMGF and this is considered within the scope of the present invention.

Accordingly, in a further aspect of the present invention there is provided a polyclonal or monoclonal antibody against BMGF.

Various procedures are known in the art which may be used for the production of antibodies to epitopes of BMGF. Various host animals may be used in the production of these BMGF antibodies following immunisation with BMGF protein including but not restricted to rabbits, mice, goats etc. Adjuvants may be used to increase the immunological response, depending on the host species, and may include but are not restricted to Freunds (complete and incomplete). BMGF monoclonal antibodies may be prepared by using techniques which enable the continuous production of antibody molecules by cell lines in vitro. These may include, but are not limited to, the hybridoma technique (Kohler and Milstein, Nature 256, 495, (1975)). Antibodies to BMGF may find use in the detection of mature and precursor forms of BMGF in various tissues, body fluids and cell lines, for example in screening assays for the growth factor, and in the affinity purification of BMGF protein.

In a still further aspect of the present invention there is provided a nucleic acid encoding BMGF or fragments thereof encoding functionally active fragments of BMGF. The nucleic acid may encode mature or precursor forms of BMGF.

Preferably the nucleic acid has the sequence shown in FIG. 5.

Due to the degeneracy of the genetic code, other nucleic acid sequences which encode the same or functionally equivalent amino acid sequence are included within the scope of the current invention. Such alterations of the BMGF nucleotide sequence may include substitutions of different nucleotides resulting in the same or a functionally equivalent gene product. Also included within the scope of this invention are nucleic acid sequences having deletions and/or additions and which result in a functionally equivalent gene product.

In a still further aspect of the present invention, there is provided a method for isolating a nucleic acid encoding BMGF or fragments thereof encoding functionally active fragments of BMGF. The nucleic acid may encode mature or precursor forms of BMGF.

The nucleic acid encoding BMGF may be obtained from cell sources that produce BMGF activity. For example, kidney cells may be used as the source of the nucleic acid. The nucleic acid encoding BMGF is preferably obtained by (but is not restricted to) reverse transcription of BMGF mRNA into complementary cDNA and subsequent Polymerase Chain reaction (PCR) amplification using oligonucleotide primers containing nucleic acid sequences encoding portions, preferably the extreme N and C terminal portions of the mature or precursor protein. Preferably the oligonucleotide primers have the following sequences or substantially homologous sequences:

5' ATC TAG GTT ACC ATG GAT GGG AAT TCA ACC AGA 3' (SEQ ID NO:10)

5' ATC TAG GTT ACC GGC GAT GGG AAT TCA ACC AGA 3' (SEQ ID NO:11)

5' CTA GAT AAG CTT TCA TCA GTA AAA CAA GTC AAC TCT 3' (SEQ ID NO:12)

Preferably the oligonucleotide primers include restriction enzyme sites to facilitate directional cloning of the nucleic acid.

More preferably, the primers include the following nucleotide sequence:

5' GGG AAT TCA ACC AGA 3' (SEQ ID NO:13)

5' GTA AAA CAA GTC AAC TCT 3' (SEQ ID NO:14).

Most preferably, the primers are:

5' GGG AAT TCA ACC AGA AGT CCT GAA 3' (SEQ ID NO:15)

5' GTA AAA CAA GTC AAC TCT CTC ACA CCT 3' (SEQ ID NO:16)

Thus, in a preferred form of this aspect of the invention there is provided a method for isolating a nucleic acid encoding BMGF or fragments thereof encoding functionally active fragments of BMGF, said method including providing a source of cells having BMGF activity;

treating the cells to obtain mRNA therefrom;

treating the mRNA thus obtained to produce cDNA therefrom; and amplifying the cDNA thus obtained by PCR using oligonucleotide primers to produce the nucleic acid.

Other methods, well known to those in the art, for obtaining nucleic acids encoding proteins exist, and the use of these methods to obtain nucleic acids encoding mature or precursor forms of BMGF is also included within the scope of the current invention. These methods may include (but are not restricted to) either chemically synthesising the nucleic acid from knowledge of the nucleic acid or amino acid sequence of the mature and/or precursor forms of BMGF or screening a cDNA and/or genomic library, preferably a bovine library, with isotopically or non-isotopically labelled nucleic acid sequences homologous to nucleotide sequence encoding part or all of the mature and/or precursor forms of BMGF.

Using standard techniques of recombinant DNA technology, well known to those skilled in the art, the nucleic acid encoding the mature or precursor forms of BMGF may be cloned into an appropriate vector, for example an expression vector.

Accordingly, in a further aspect of the present invention there is provided a vector including a nucleic acid encoding BMGF or fragments thereof encoding functionally active fragments of BMGF.

The nucleic acid may encode mature or precursor forms of BMGF.

Preferably the nucleic acid has the sequence shown in FIG. 5.

A large number of vector-host systems are available and these include (but are not restricted to) plasmids such as pBR322 or pUC derivatives, or bacteriophage such as lambda derivatives.

The vector of the present invention may be used to express recombinant BMGF in host cells.

Accordingly in a still further aspect of the present invention there is provided recombinant BMGF.

The recombinant BMGF may be in a substantially pure form. Preferably it is at least about 70% pure, more preferably at least about 90% pure, most preferably at least about 99% pure. The recombinant BMGF may have a molecular weight of approximately 9 kDa in the nonglycosylated form as determined by SDS-PAGE. It may have the ability to stimulate the proliferation of fibroblasts and/or epithelial cells and/or osteoblast cells.

In a preferred form of this aspect of the invention the BMGF has an amino acid sequence as follows:
DGNSTRSPEDDGLLCGDHAENC-PATTTQPKRRGHFSRCPKQYKHYCIKGR-CRFVVAEQTPSCVCDEGYAGARCERVDLFY (SEQ ID NO:2)

The present invention also includes within its scope precursor forms of recombinant BMGF and functionally active fragments (peptides) of recombinant BMGF.

In a preferred form of this aspect of the invention the fragments of BMGF may include the following amino acid sequences or substantially homologous sequences:
DGNSTRSPEDDGLLCGDHAENCPATTTQPKRRGHF (SEQ ID NO:3)
GYAGARCERVDLFY (SEQ ID NO:4); or
DGNSTRSPEDDGLLCGDHAENCPATTTQPK (SEQ ID NO:5); or
RRGHFSRCPK (SEQ ID NO:6); or
QYK (SEQ ID NO:7); or
HYCIK (SEQ ID NO:8); or
GRCRFVVAEQTPSCVCDEGYAGARCERVDLFY (SEQ ID NO:9).

The present invention also provides a method for producing recombinant BMGF, said method including
providing a vector including a nucleic acid encoding BMGF or fragments thereof encoding functionally active fragments of BMGF; and
a host cell;
introducing said vector into said host cell;
expressing said recombinant BMGF; and
isolating said recombinant BMGF.

The vector may be introduced into the host cell by methods such as (but not restricted to) transformation, transfection, electroporation and infection. Host cells may include but are not restricted to bacteria such as *E.coli* cells.

The recombinant BMGF may be expressed as a fusion protein. The fusion proteins formed according to this aspect of the present invention, may be isolated as inclusion bodies within the host cell.

It will be understood that the recombinant BMGF so formed may be isolated, preferably following disruption of the host cell, by conventional methods of polypeptide purification well known to those skilled in the art, utilising techniques such as ion-exchange chromatography, size-exclusion chromatography, affinity chromatography, reverse-phase high performance liquid chromatography and/ or if necessary further purification processes. The recombinant BMGF may be isolated as a fusion protein or cleaved from its fusion partner using conventional methods well known to those in the art.

In a preferred form of this aspect of the invention, the recombinant BMGF may be prepared as a fusion protein according to Australian Patent 633099 to the applicant, the entire disclosure of which is incorporated herein by reference, wherein a portion of porcine growth hormone is linked to the N-terminal sequence of BMGF, optionally through a cleavable sequence.

The BMGF of the present invention, including the naturally-derived mature or precursor forms of BMGF, and recombinant BMGF protein isolated as either the mature or precursor form with or without its fusion partner (and mutants, analogues, fragments and derivatives thereof) may be utilised:

in the growth and/or proliferation of mammalian cells and more organised structures such as skin in vitro either alone or in combination with other factors (such as or not restricted to IGF-I or IGF-I analogues) or, for example as a supplement to foetal serum in the enhancement of wound healing and/or tissue repair, eg. in the treatment of surface wounds, either alone or in combination with other factors in the prevention, amelioration or treatment of conditions associated with impaired gut barrier function, such as inflammatory bowel disease and mucosal immunity, either alone or in combination with other factors as a supplement in infant milk formulae in the prevention, treatment or amelioration of peridontal disease in cosmetic applications.

Accordingly, the present invention provides a composition for promoting the growth and/or proliferation of mammalian cells and tissues, said composition including an effective amount of BMGF, or mutants, analogues and derivatives of BMGF, precursor and fusion protein forms of BMGF and functionally active fragments (peptides) of BMGF; together with a culture medium, preferably a defined culture medium.

The present invention also provides a method for promoting the growth and/or proliferation of mammalian cells and tissues, said method including growing said cells or tissues in a culture medium including an effective amount of BMGF, or mutants, analogues and derivatives of BMGF, precursor and fusion protein forms of BMGF and functionally active fragments (peptides) of BMGF.

The term "effective amount" as used herein in methods of use for BMGF means an amount sufficient to elicit a statistically significant response at a 95% confidence level ($p<0.05$ that the effect is due to chance alone).

In a further aspect of the present invention there is provided a method for promoting the growth and/or proliferation of mammalian cells and tissues, said method including growing said cells or tissues in a culture medium including an effective amount of BMGF, or mutants, analogues and derivatives of BMGF, precursor and fusion protein forms of BMGF and functionally active fragments (peptides) of BMGF, together with an effective amount of an IGF that produces a synergistic response.

The IGF or insulin-like growth factor that is included in the culture medium of this further aspect of the present invention may be IGF-I, IGF-II or a functionally effective mutant or analogue of IGF such as $LR^3IGF-1$ described in Australian Patent 633099 to the applicant.

In a further aspect of the present invention there is provided a composition for the treatment of surface wounds, said composition including an effective amount of BMGF, or mutants, analogues and derivatives of BMGF, precursor and fusion protein forms of BMGF and functionally active fragments (peptides) of BMGF; together with a pharmaceutically acceptable excipient, diluent or carrier The present invention also provides a method for enhancing wound healing and/or tissue repair, said method including administering to a patient in need thereof an effective amount of BMGF, or mutants, analogues and derivatives of BMGF, precursor and fusion protein forms of BMGF and functionally active fragments (peptides) of BMGF.

There are no limitations on the type of wound that may be treated, and these may include (but are not restricted to): surface ulcers (eg. pressure, venous stasis, diabetic and atherosclerotic ulcers), burns or accidental wounds (such as lacerations and incisions) and wounds to epithelial lined organs such as the stomach and intestine (large and small) and corneal injury to the eye. The application of BMGF to wound sites may be in the form of (but is not restricted to) a powder, gel, ointment or bandages and other wound dressings incorporating BMGF. The BMGF may be applied to wounds either alone or in a mixture including other growth factors, and may be in combination with other ingredients, such as adjuvants, carriers and solubilising agents. The concentration of BMGF in the composition is not critical but should be enough to induce cell proliferation, particularly epithelial cell proliferation.

The gastrointestinal tract (gut) is constantly challenged by potentially harmful substances present in the intestinal lumen and subsequently, maintenance of a normal mucosal barrier is crucial in both adult and infant life. Barrier function may be compromised by damage to the epithelial surface, for example as occurs during highdose chemotherapy, infection and trauma. In addition, a pro-inflammatory response, generated after sensitisation to normal and luminal antigens, may lead to epithelial damage and increased permeability. This immune dysfunction is thought to play a significant role in the pathogenesis of disorders including coeliac and inflammatory bowel disease. Given the epithelial-cell stimulatory activity of BMGF, a still further application of the present invention is in the treatment, amelioration or prevention of conditions associated with impaired gut function, such as inflammatory bowel disease and mucosal immunity, either alone or in combination with other growth factors, preferably as an enteral formulation.

Accordingly, in a still further aspect of the present invention there is provided a composition for the prevention, amelioration or treatment of conditions associated with impaired gut function, said composition including an effective amount of BMGF, or mutants, analogues and derivatives of BMGF, precursor and fusion protein forms of BMGF and functionally active fragments (peptides) of BMGF; together with a pharmaceutically acceptable excipient, diluent or carrier.

The present invention also provides a method for preventing, ameliorating or treating conditions associated with impaired gut function, said method including administering to a patient in need thereof an effective amount of BMGF, or mutants, analogues and derivatives of BMGF, precursor and fusion protein forms of BMGF and functionally active fragments (peptides) of BMGF.

The present invention also provides a method for preventing or treating periodontal disease said method including administering to a patient in need thereof an effective amount of BMGF, or mutants, analogues and derivatives of BMGF, precursor and fusion protein forms of BMGF and functionally active fragments (peptides) of BMGF.

There is also provided a use of BMGF in a cosmetic application, said use including administering to a patient in need thereof an effective amount of BMGF, or mutants, analogues and derivatives of BMGF, precursor and fusion protein forms of BMGF and functionally active fragments (peptides) of BMGF.

The present invention also provides an infant formula including BMGF, or mutants, analogues and derivatives of BMGF, precursor and fusion protein forms of BMGF and functionally active fragments (peptides) of BMGF; together with nutrient components. Preferably the infant formula is a milk formula.

Throughout the description and claims of this specification, the word "comprise" and variations of the word, such as "comprising" and "comprises", is not intended to exclude other additives, components, integers or steps.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1 bovine cheese whey extract (GFE-2) prepared according to Australian Patent AU645589 was subjected to acidification and ultrafiltration and a series of chromatographic steps. The figure illustrates the elution profile of protein and activity in an EGF-receptor binding assay following each chromatographic step.

FIG. 2 illustrates SDS-PAGE of BMGF. Purified preparation of BMGF was analysed with a Pharmacia Phastsystem on a 8–25% pre-cast phast gel under reducing (R) or non-reducing (N) conditions then visualised with silver stain. The numbers on the left of each figure represent the migration positions of size standards; 94 kDa, phosphorylase b; 67 kDa, albumin; 43 kDa, ovalbumin; 30 kDa, carbonic anhydrase; 20.1 kDa, trypsin inhibitor; 14.4 kDa, α-lactalbumin.

FIG. 3 illustrates amino acid sequence determination of BMGF. X indicates an amino acid that was not identified by amino-terminal sequencing. Deduced Sequence: SEQ ID NO:2. N-terminal sequence: SEQ ID NO:18. Endoproteinase Lys-C peptides: SEQ ID NOS:19 and 6–9.

FIG. 5 illustrates nucleotide sequence (SEQ ID NO:1) and deduced amino acid sequence (SEQ ID NO:2) of BMGF.

FIG. 8 illustrates effect of BMGF on the proliferation of a variety of cultured cell lines. Cell proliferation is shown as the response to increasing concentrations of BMGF and is expressed as the percent increase above cells incubated in the absence of BMGF. Balb/c 3T3 cells and DECO cells were incubated with increasing concentrations of BMGF in the presence or absence of an insulin-like growth factor-I analogue (LR$^3$IGF-1) at a concentration of 50 ng.m$^{-1}$.

Figure 9:
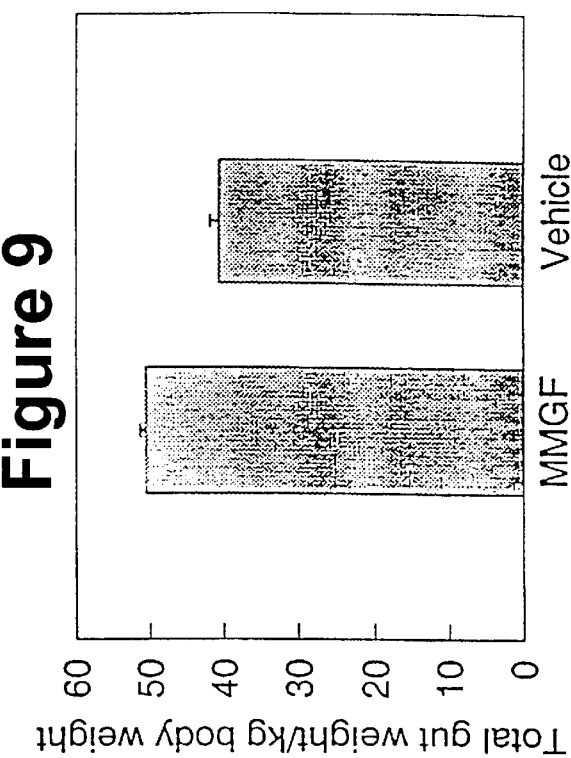

FIG. 9 illustrates weight of the gastrointestinal tract relative to total body weight (g/kg) of Sprague-Dawley rats following infusion of BMGF (500 μg/kg/day) or vehicle (0.1 M acetic acid) for 7 days.

EXAMPLES

Example 1

Isolation of BMGF from Bovine Cheese Whey Extract

Step 1: Ultrafiltration Size Exclusion

6 L of bovine cheese whey extract (GFE-2 prepared according to that outlined in AU645589) (protein concentration=40 mg.ml$^{-1}$) is acidified to pH 2.5 with HCl and then microfiltered against a 100 kDa polysulfonate exclusion membrane fitted to a Sartorius Sartocon II cross-flow filtration unit (Sartorius, Gottingen, Germany). The permeate obtained from this step is then diafiltered using an Amicon DC-10 ultrafiltration unit (Amicon, Danvers, Mass.) equipped with a 0.1 μm hollow fibre cartridge and then concentrated to approximately 1.8 L against a 3 kDa cellulose triacetate membrane using the same unit.

Step 2: Anion Exchange Chromatography

Figure 1F:
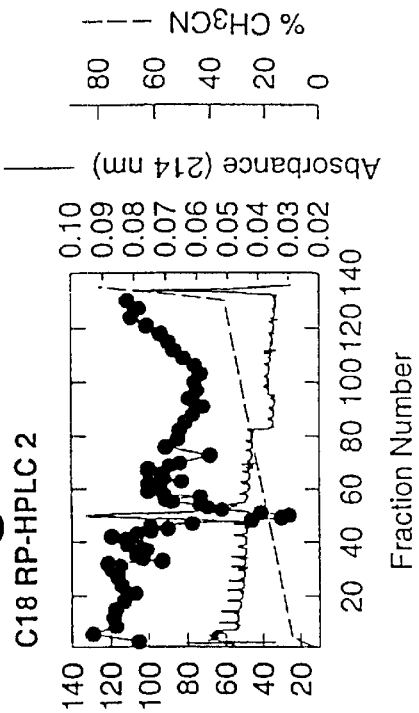
Figure 1E:
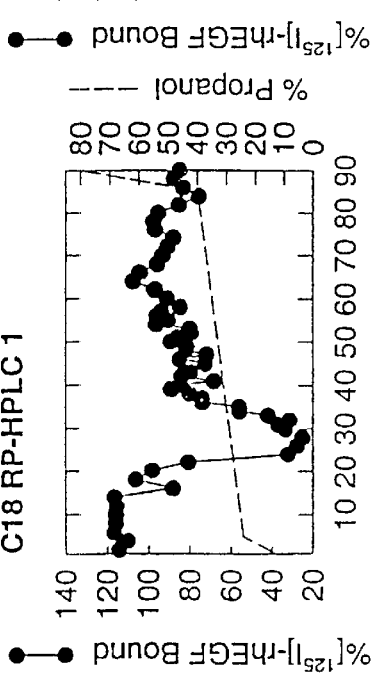

The desalted and concentrated permeate is made 20 mM Tris-HCl (pH 7.5) with solid Trs Base and pH adjustment to 7.5 with 5 M HCl, filtered through a 1 μm membrane, and applied to a Q-Sepharose column (5×15 cm; Pharmacia, Sweden) attached to an FPLC system (Pharmacia, Sweden) at a flow rate of 5 ml.min$^{-1}$. The column is then washed with 20 mM Tris-HCl and the proteins that remain bound to the column (which include BMGF) are eluted with a 2.1 L linear salt gradient of 0–0.6 M NaCl in 20 mM Tris-HCl at a flow rate of 5 ml min$^{-1}$. Fractions of 30 ml are collected and analysed for BMGF activity (FIG. 1). Activity was measured as Epidermal Growth Factor (EGF) Receptor Binding Activity. Fractions containing BMGF are pooled and then dialysed for 16 h against H$_2$O (2×20 L) followed by freeze-drying.

EGF-receptor Binding Assay

BMGF was measured by competition for [$^{125}$I]-rhEGF binding to specific EGF receptors present on AG2804 fibroblasts. Briefly, AG2804 cells were grown to 70–80% confluence in DMEM supplemented with 10% FBS in 24-well plates. The cells were washed twice with binding buffer (100 mM Hepes pH 7.6, 120 mM NaCl, 5 mM KCl, 1.2 mM M$_g$SO$_4$.7H$_2$O, 8 mM glucose, and 0.1% BSA) and then incubated with column fractions and [$^{125}$I]-rhEGF (10 000 cpm) in binding buffer for 18 h at 4° C. At the end of this period, cells were washed three times with Hanks buffered salt solution (HBSS) and lysed with 1 ml of 0.5 M NaOH, 0.1% Triton X-100 for 30 min at room temperature. Radioactivities of cell lysates were determined with a gamma counter. Total binding was determined by adding binding buffer in place of column fractions. Non-specific binding was determined by adding an excess (100 ng) of unlabelled rhEGF in place of sample and was usually about 5% of total binding. Standard curves for EGF competition were obtained by using increasing amounts of unlabelled rhEGF (0.2–100 ng) in the assay.

Step 3: Gel/filtration Chromatography

The freeze-dried BMGF pool from the above step is reconstituted in 15 ml 150 mM NaCl, 1 M glacial acetic acid, and 10% (v/v) CH$_3$CN, filtered through a 0.22 μm membrane and applied to a Superdex-75 35/600 (3.5×60 cm, Amersham Pharmacia Biotech, Sydney, Australia) column attached to the FPLC at a flow rate of 3.5 ml.min$^{-1}$. Fractions of 17.5 ml are collected and analysed for BMGF activity (FIG. 1).

Step 4: C4 RP-HPLC

Fractions containing BMGF activity are pooled, diluted 1:4 with 0.1% TFA and applied to a Delta-Pack C4 RP-HPLC column (15 μm, 300 Å, 25×100 mm, Millipore-Waters, Lane Cove, New South Wales, Australia) equilibrated with 0.1% TFA. The column is washed extensively with 0.1% TFA and bound protein then eluted with a linear gradient of 0–80% CH$_3$CN and 0.08% TFA over 80 min at a flow rate of 5 ml.min$^{-1}$. Fractions of 10 ml are collected and those containing BMGF activity (FIG. 1) pooled and freeze-dried.

Step 5: Affinity Chromatography

The freeze-dried pool from the above step is reconstituted in 20 ml of 20 mM Tris-HCl (pH 7.5) and applied to a 5 ml HiTrap Heparin-Sepharose affinity column (Amersham Pharmacia Biotech, Sydney, Australia) attached to the FPLC at a flow rate of 0.5 ml.min$^{-1}$. The column is washed with 20 mM Tris-HCl (pH 7.5) until the O.D.$_{280\ nm}$ returns to baseline and bound proteins are then eluted with 75 ml of a linear salt gradient of 0–1M NaCl in 20 mM Tris-HCl (pH 7.5) (FIG. 1). Fractions of 1 ml are collected and those containing BMGF activity pooled.

Step 6: C18 RP-HPLC #1

The Heparin-Sepharose pool is diluted 1:4 with 10% propanol, 0.13% HFBA and applied to a Nova-Pack C18 RP-HPLC column (4 μm, 60 Å, 8×100 mm, Millipore-Waters, Lane Cove, New South Wales, Australia) at a flow rate of 1 ml.min$^{-1}$. The column is washed with 10% propanol, 0.13% HFBA and bound protein eluted with a two-step gradient of 10–24% propanol, 0.13% HFBA over 10 min and then 24–40% propanol, 0.13% HFBA over 160 min. 1 ml fractions are collected and analysed for BMGF activity (FIG. 1).

Step 7: C18 RP-HPLC #2

Fractions containing BMGF activity from the above step are pooled, diluted 1:3 with 0.1% TFA and applied to the same column as above at a flow rate of 1 ml.min$^{-1}$. The column is washed with 0.1% TFA and bound protein eluted with a two step gradient of 0–10% CH$_3$CN over 10 min and then 10–35% CH$_3$CN over 250 min at a flow rate of 1 ml.min$^{-1}$ (FIG. 1). 2 ml fractions are collected and analysed for BMGF activity. The fractions containing BMGF activity are pooled and stored at −20° C. until required.

Figure 2:
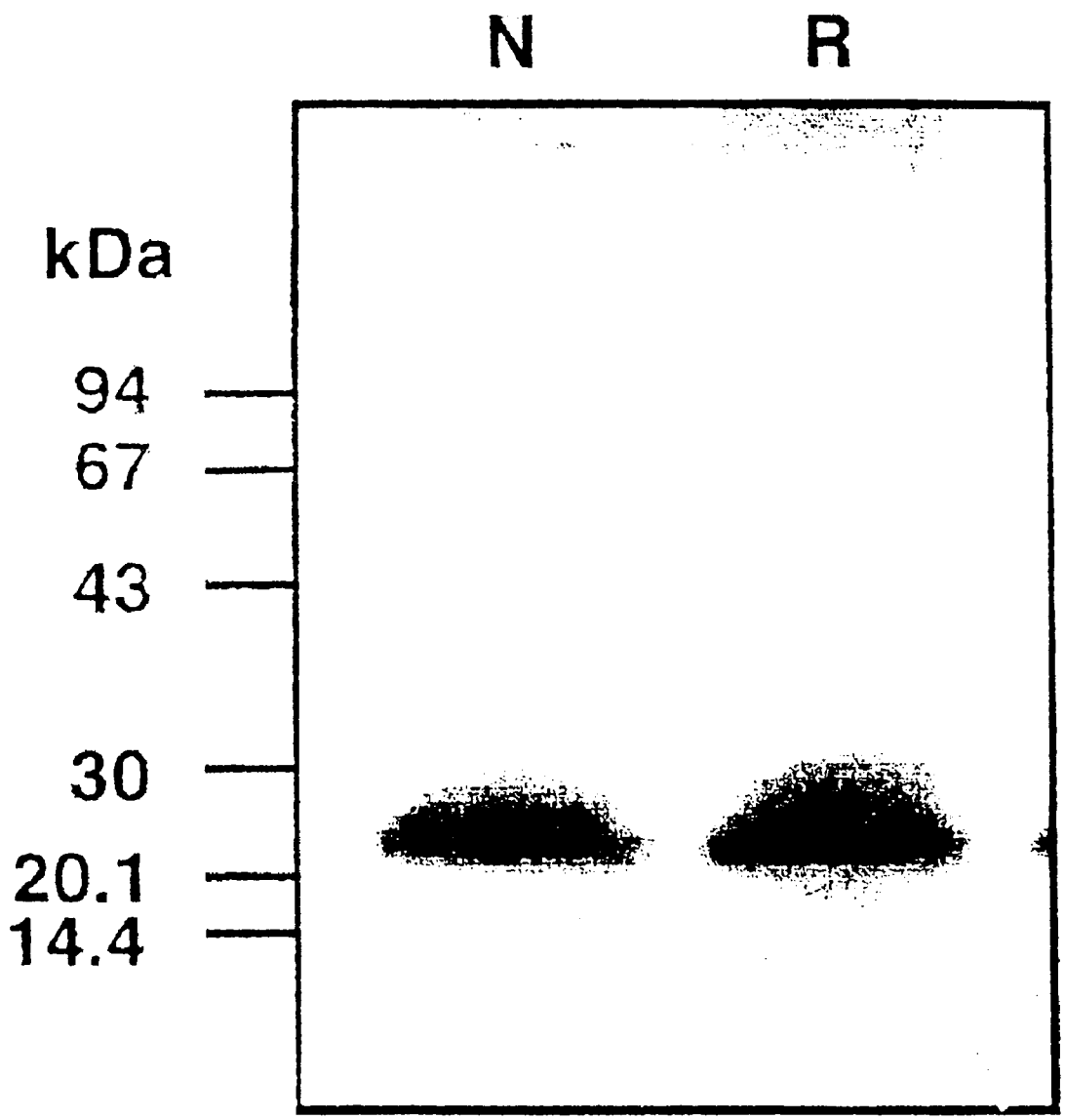

A summary of the result of purification is shown in Table 1. The BMGF is present in the active fractions from the final C18 RP-HPLC step in a form which is up to, and including, 99% pure and has a molecular weight of approximately 21–25 kDa. These criteria being estimated from silver stained 8–25% gradient SDS-PAGE gels run on the Pharmacia Phast system (see FIG. 2) and by N-terminal sequence analysis.

TABLE 1

Summary of the purification of BMGF

| Purification Step | Total Protein mg | Activity[a] Units | Specific Activity Units/mg | Purification-fold | Yield % |
|---|---|---|---|---|---|
| GFE-2 | 209559[b] | 5365.7 | 0.025 | 2 | 100.0 |
| Permeate | 16326[b] | 2808.0 | 0.172 | 7 | 52.3 |
| Q-Sepharose | 2820[b] | 924.9 | 0.328 | 13 | 17.2 |
| Superdex-75 | 228[b] | 372.2 | 1.630 | 63 | 6.9 |
| C4 RP-HPLC | 16.5[b] | 157.6 | 9.502 | 371 | 2.9 |
| Heparin Sepharose | 0.372[c] | 138.7 | 376.0 | 14687 | 2.5 |
| C18 RP-HPLC#1 | 0.152[c] | 48.0 | 320.0 | 12500 | 0.9 |
| C18 RP-HPLC#2 | 0.029[d] | 27.7 | 957.6 | 37406 | 0.5 |

[a]One unit of activity is defined as the amount of factor required to compete for 50% of the binding of [$^{125}$I]-rhEGF to AG2804 cells.
[b]Estimated by BCA Protein assay kit (Pierce).
[c]Estimated by micro BCA Protein assay kit (Pierce).
[d]Estimated by N-terminal sequence analysis.

Example 2

N-terminal and Peptide Sequence Analysis of BMGF

The amino acid sequence of bovine BMGF and of peptide fragments generated by Endoproteinase Lys-C digestion was determined using a Hewlett-Packard G1000A protein sequencer. Twenty μg of purified BMGF was reduced with 100 μl 4 mM DTT in 400 μl of denaturation buffer (6 M guanidine-HCl, 100 mM Tris-Cl pH 8.5, and 5 mM EDTA) for 30 min at room temperature in the dark. The denatured and reduced BMGF was S-carboxymethylated by adding 1 μmol of iodoacetic acid containing 200 μCi of iodo[2-$^3$H]

acetic acid in denaturation buffer and incubated as above. Subsequently 16 μmol of iodoacetic acid dissolved in denaturation buffer was added, and the incubation continued for a further 15 min. The reaction was stopped by the addition of 5 μl TFA and the [$^3$H]carboxymethylated BMGF recovered by RP-HPLC. The [$^3$H]carboxymethylated BMGF was dried under vacuum and sequenced from the N-terminus or digested with endoproteinase Lys-C (0.5 μg, Promega) in 100 μl Tris-HCl (pH 8.5) at 37° C. for 16 h. The reaction was stopped by the addition of 5 μl TFA and the resulting peptide fragments separated on a C18 RP-HPLC column (2.1×30 mm, Brownlee Lab, Santa Clara, Calif.) using a linear gradient of 0–50% CH$_3$CN and 0.08% TFA over 70 min at a flow rate of 0.25 ml.min$^{-1}$. Peptide-containing fractions were dried under vacuum and sequenced (FIG. 3).

Example 3

Deglycosylation of BMGF

Figure 4:
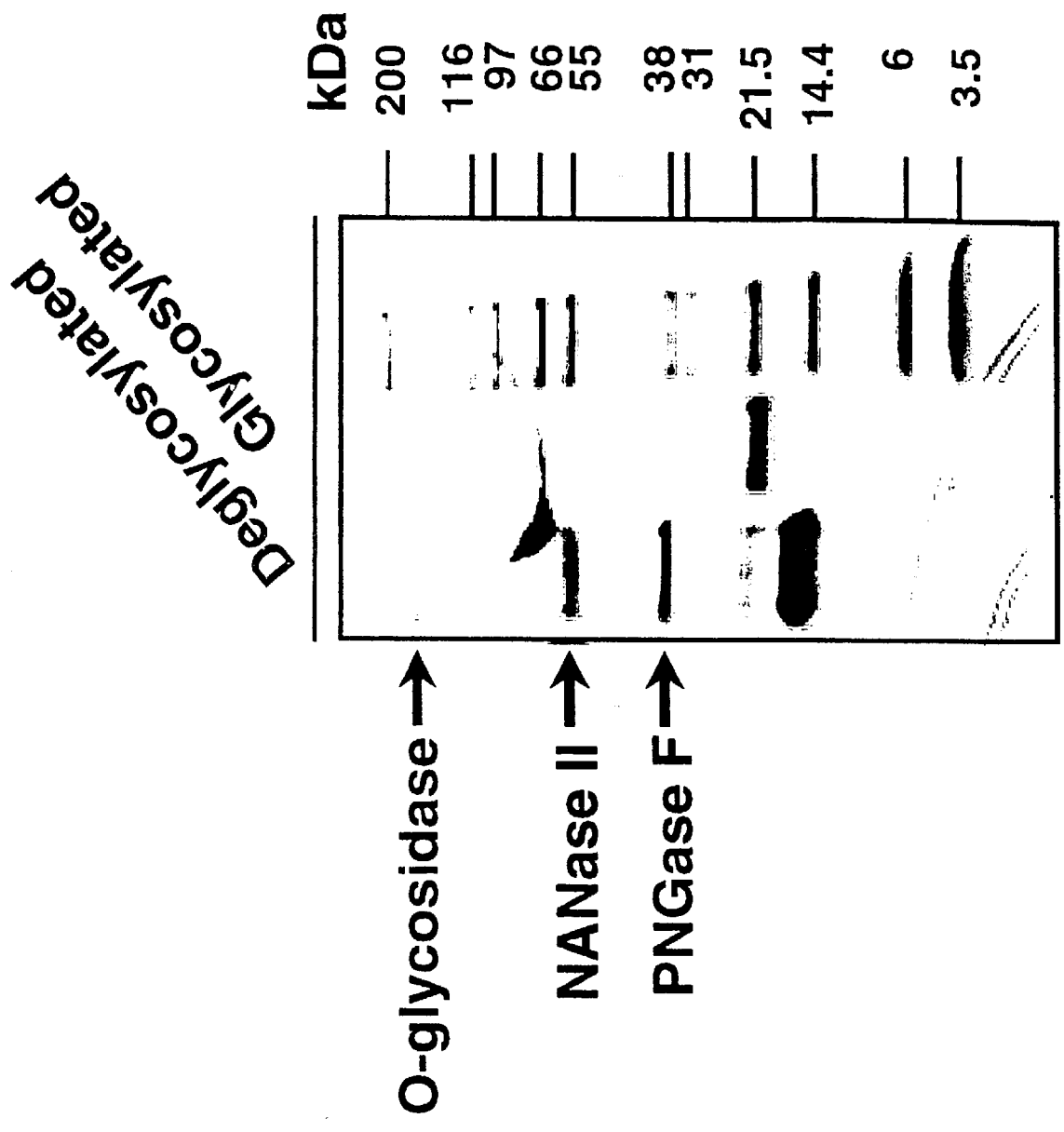
FIG. 4 illustrates deglycosylation of BMGF. Purified BMGF was incubated in the presence and absence of NANase II, O-glycosidase DS and PNGaseF, and analysed by SDS-PAGE on a 10–20% Tricine gel (see example 3 for details).

10 μg pure BMGF was dried in a 1.5 ml polypropylene microfuge tube, resuspended in 16 μl 50 mM sodium phosphate (pH 6.0), and 0.2 units α2-3,6-Neuraminidase (NANase II) and 0.002 units Endo α-acetylgalactosaminidase (O-glycosidase DS) (BioRad, Richmond, Calif.) added and the reaction incubated at 37° C. for 1 h. The reaction volume was then increased to 40 μl with 500 mM sodium phosphate (dibasic) and 2.5 μl 2% SDS, 1 M β-mercaptoethanol added. The reaction was then heated to 95° C. for 5 min. placed on ice and then 2.5 μl Nonidet-P40 and 0.005 units Peptide-N$^4$(acetyl-β-glucosaminyl)-asparagine aminidase (PNGase F) (BioRad, Richmond, Calif.) added and incubated at 37° C. for 3 h. The reaction was then dried under vacuum, resuspended in SDS-PAGE reducing buffer and run on a 10–20% Tricine gel (Novex) (FIG. 4).

Example 4

Cloning of the Mature Form of BMGF

Two oligonucleotide primers (see below) corresponding to the N- and C-terminal amino acid sequences of BMGF (see example 2) were chemically synthesised and used to amplify by PCR (Polymerase Chain Reaction) the nucleotide sequence encoding the complete mature form of bovine BMGF.
Primer 1: 5' GAT GGG AAT TCA ACC AGA AGT CCT GAA 3' (SEQ ID NO:17)
primer 2: 5'GTA AAA CAA GTC AAC TCT CTC ACA CCT 3' (SEQ ID NO:16)

Total RNA was isolated from 80–90% confluent Madin-Darby bovine kidney cells (MDBK, ATCC CCL 22) using a RNeasy Mini kit (Qiagen, Clifton Hill, Victoria, Australia). cDNA was synthesised from 1 μg total MDBK RNA using oligo dT primer and Superscript II (Life Technologies, Melbourne, Australia). The subsequent cDNA was used as a template for PCR with the above primers. PCR was carried out in 50 μl of 60 mM Tris-SO$_4$, 18 mM (NH$_4$)$_2$SO$_4$, 1.5 mM MgSO$_4$ (pH 9.1), 0.2 mM dNTPs, 200 ng each primer, 1 U eLONGase (Life Technologies, Melbourne, Australia) and 1 ul cDNA. Following an initial incubation at 94° C. for 3 min. 30 cycles of amplification were carried out as follows: 94° C. for 1 min. 50° C. for 1 min. and 68° C for 1 min. followed by a final 3 min extension at 68° C.

The PCR reaction was analysed by electrophoresis through a 2% agarose gel and a 240 bp product excised from the gel and purified using a Promega PCR Preps Purification kit. The purified PCR product was blunt-end ligated into the vector pCR-Blunt (Invitrogen) according to the manufacturer's instructions. BMGF vector constructs were transformed into E. coli TOP10 (Invitrogen) cells and selected on LB agar plates containing 50 μg ml$^{-1}$ kanamycin. The complete nucleotide sequence of mature BMGF (see FIG. 5) was determined by the dideoxy chain termination method (Sanger et al. Proc. Natl. Acad. Sci. U.S.A. 74, 5463, (1977)) using an Amplicycle sequencing kit (Perkin-Elmer) and universal M13 forward (-40) and reverse primers.

Example 5

Construction of BMGF cDNA Expression Plasmid of E. coli

Figure 6:
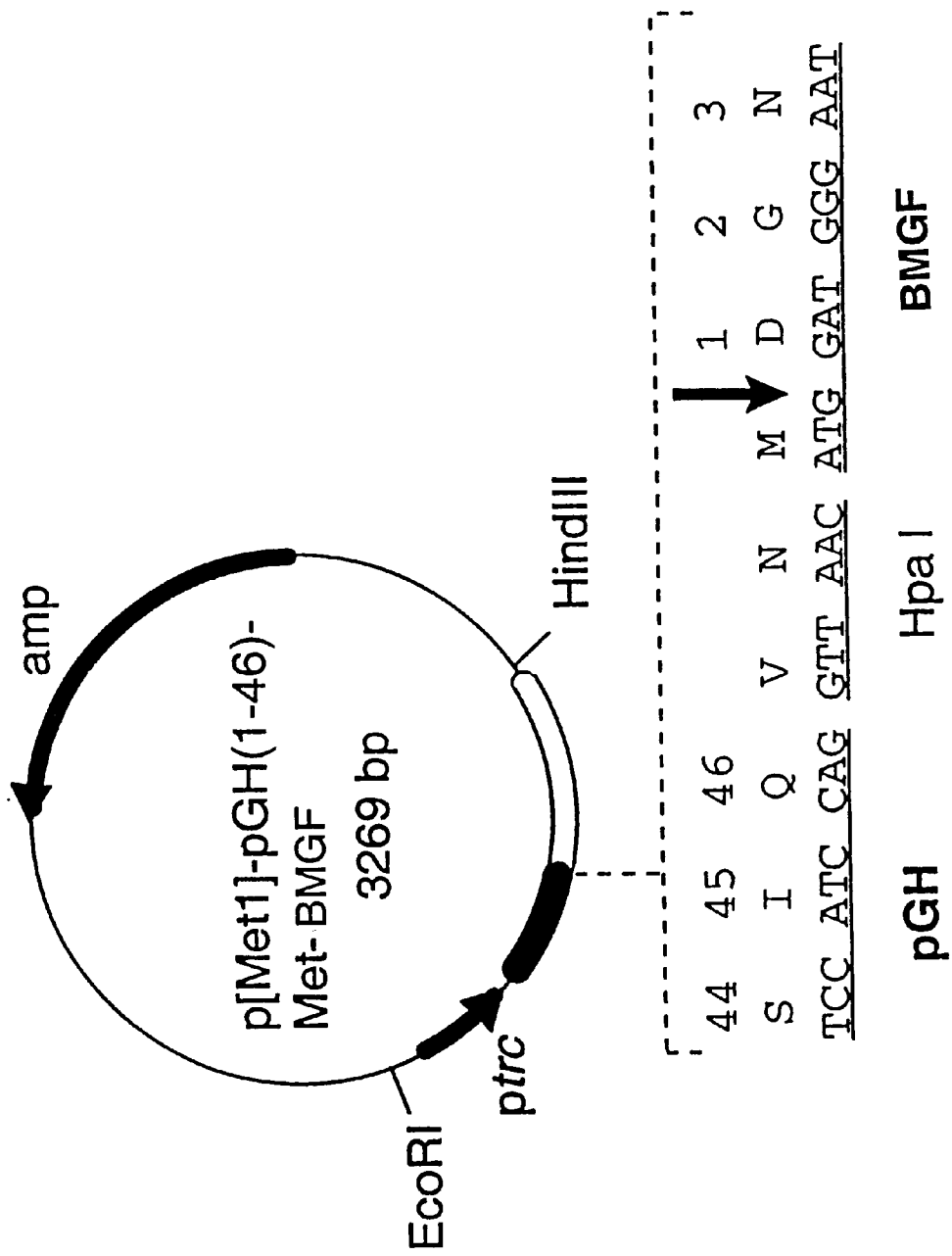
FIG. 6 illustrates construction of the pGH(1–46)-Met-BMGF expression vector. The arrow indicates the site for cyanogen bromide cleavage to produce authentic BMGF. (SEQ ID NOS:21–22)

To obtain the DNA encoding the complete 80 amino acids of mature BMGF [Asp$^1$-Tyr$^{80}$] for expression vector construction, total RNA was isolated from 80–90% confluent Madin-Darby bovine kidney cells (MDBK, ATCC CCL 22) using an RNeasy Mini kit (Qiagen, Clifton Hill, Victoria, Australia). cDNA was synthesised from 1 μg total MDBK RNA using oligo dT primer and Superscript II (Life Technologies, Melbourne, Australia). The subsequent cDNA was used as a template for PCR with the primers shown below. The PCR conditions were the same as described above.
Primer 1: 5'ATC TAG <u>GTT ACC</u> ATG GAT GGG AAT TCA ACC AGA 3' (SEQ ID NO: 11)
  Underlined: Bpa I restriction enzyme site
  Double underline: Methionine site for cleavage with cyanogen bromide
  Bold: nucleotide sequence of amino acids 1–6 of BMGF
Primer 2: 5' CTA GAT <u>AAG CTT</u> TCA TCA GTA AAA CAA GTC AAC TCT 3' (SEQ ID NO:12)
  Underlined: HIND iii restriction enzyme site
  Double underlined: two stop codons
  Bold: nucleotide sequence of amino acids 75–80 of BMGF The PCR reaction was analysed by electrophoresis through a 2% agarose gel and a 273 bp product excised from the gel and purified using a Promega PCR Preps Purification kit. The purified PCR product and the plasmid p[Met$^1$]-pGH (1–46) were digested with the restriction enzymes Hpa I and Hind III (New England Biolabs) and the digested PCR product ligated into linearised p[Met$^1$]-pGH(1–46) with T4 DNA ligase (Promega) (FIG. 6). p[Met$^1$]-pGH(1–46) is an expression vector (owned and patented by GroPep Pty Ltd) which contains the nucleotide sequence encoding the first 46 amino acids of methionyl porcine growth hormone downstream of the strong tee promoter. Vector constructs were transformed into E. coli JM101 (lacq) and selected on LB agar plates containing 50 μG ml$^{-1}$ ampicillin.

Example 6

Purification of Authentic BMGF Produced by an E. coli Transformant

The E. coli JM101 strain harbouring the plasmid [Met$^1$]-pGH(1–46)-Met-BMGF was selected as a single colony and used to inoculate a 20 ml starter culture consisting of 60 mM K$_2$HPO$_4$, 33 mM KH$_2$PO$_4$, 7.5 mM (NH$_4$)$_2$SO$_4$, 1.7 mM sodium citrate, 10 μM MgSO$_4$.7H$_2$O, 0.2% D-glucose, 0.0005% thiamine and 50 μg ml$^{-1}$ ampicillin. The culture was grown at 37° C. for 16 h. The starter culture was then in turn used to inoculate two 5 L fermenters (Applicon) containing in each 3 L of growth medium (30 mM NH$_4$Cl, 7 mM $K_2SO_4$, 12 mM $KH_2PO_4$, 19 mM $Na_2HPO_4$, 139 mM D-glucose, 2.4 mM $MgSO_4.7H_2O$, 0.0004% thiamine, 0.035 mM $Fe(II)SO_4.7H_2O$, 0.0074 mM $MnSO_4.7H_2O$, 0.0008 mM $CuSO_4.7H_2O$, 0.074 mM tri-sodium citrate and 50 ug.ml$^{-1}$ ampicillin pH 6.9). Bacteria were grown at 37° C. until the absorbance at 600 nm reached an O.D. of 4.0 and then induced with 0.33 mM IPTG and the cultivation was continued until glucose became limiting indicated by a sharp rise in pH. Regulation of temperature, pH and oxygen was under automatic control (FC4 Data system, Real Time Engineering). Cells were disrupted at 5000 p.s.i. following five passes through a Rannie homogeniser and inclusion bodies collected by centrifugation (10 000 rpm, 25 min. 4° C.). The inclusion bodies were washed twice with 30 mM NaCl, 10 mM $KH_2PO_4$, 0.5 mM $ZnCl_2$ by centrifugation at 6000 rpm and stored at −80° C.

Washed inclusion bodies, in 20 g batches, were thawed, suspended at 10% (w/v) in 8 M urea, 0.1 M Tris-HCl, 40 mM glycine, 40 mM dithiothreitol and 0.5 mM $ZnCl_2$ (pH 9.0) and stirred for 30 min at room temperature. The solubilised inclusion bodies were centrifuged at 14 000 rpm for 20 min and the resultant supernatant desalted on a Pharmacia-LKB XK column packed with Cellufine GCL-1000 and equilibrated with 8 M urea, 0.1 M Tris-HCl, 40 mM glycine, 1.6 mM dithiothreitol and 0.5 mM $ZnCl_2$ (pH 9.0) at a flow rate of 2 ml.min$^{-1}$. 30 ml fractions were collected and those containing recombinant [Met$^1$]-pGH (146)-Met-BMGF fusion protein were pooled and subject to oxidative refolding by diluting the pool to a final protein concentration of 0.1 mg.ml$^{-1}$ in 4 M urea, 40 mM glycine, 0.1 M Tris-HCl, 5 mM EDTA, 0.4 mM DTT and 1 mM 2-hydroxethyl disulphide, pH 9.0. After stirring for 3 h at room temperature, the reaction was stopped by pH adjustment to 6.45 with HCl.

The refolded fusion protein was next loaded onto a Pharmacia-LKB XK50 column packed with 100 ml of Sepharose Fast Flow S (Amersham Pharmacia Biotech, Sydney, Australia) equilibrated with 8 M urea, 50 mM ammonium acetate (pH 6.45) at a flow rate of 15 ml.min$^{-1}$. The column was washed with the above buffer until $OD_{280\ nm}$ returned to baseline. The column was then eluted with a linear salt gradient of 0–0.7 M NaCl in the same buffer at a flow rate of 15 ml.min$^{-1}$. Fractions of 30 ml were collected and those containing fusion protein pooled.

The fusion protein pool was desalted and further purified by reverse-phase HPLC chromatography on a C4 Prep-Pak column (40 mm×100 mm; 300 A, 15 μm; Millipore-Waters, Lane Cove, New South Wales, Australia). The protein pool was adjusted to 0.1% TFA and loaded onto the C4 column at 50 ml.min$^{-1}$. The column was washed extensively with 0.1% TFA and protein eluted with a gradient of 18–50% (v/v) acetonitrile over 90 min in the presence of 0.08% TFA at a flow rate of 20 ml.min$^{-1}$. Fractions of 30 ml were collected and those containing fusion protein pooled and lyophilised.

Figure 7A:
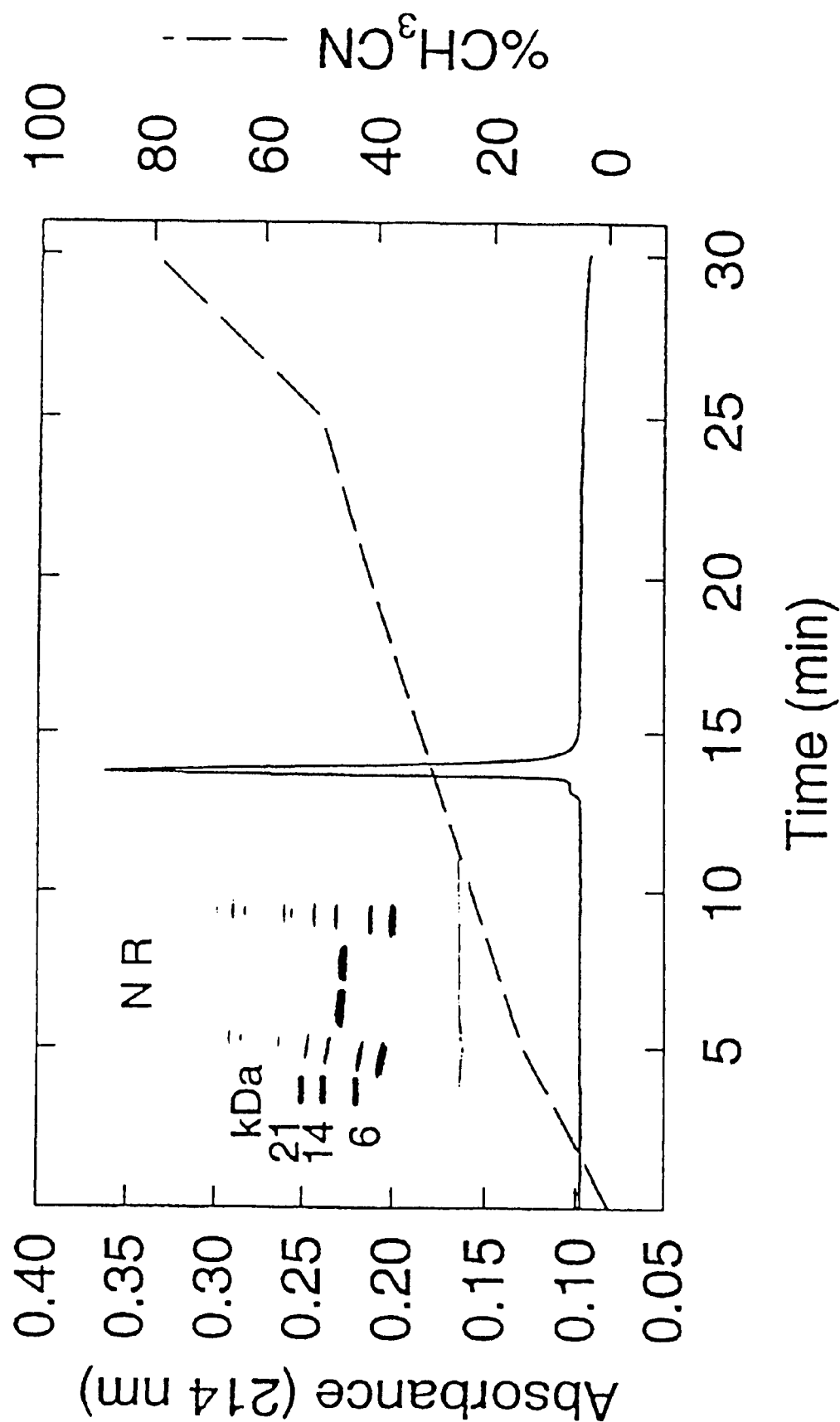
FIG. 7 illustrates C4 reverse-phase HPLC of purified recombinant authentic BMGF (A) and recombinant pGH (1–46)-Met BMGF fusion protein (B). Insets: SDS-PAGE analysis of the purified preparations under reducing (R) or non-reducing conditions (N).
Figure 7B:
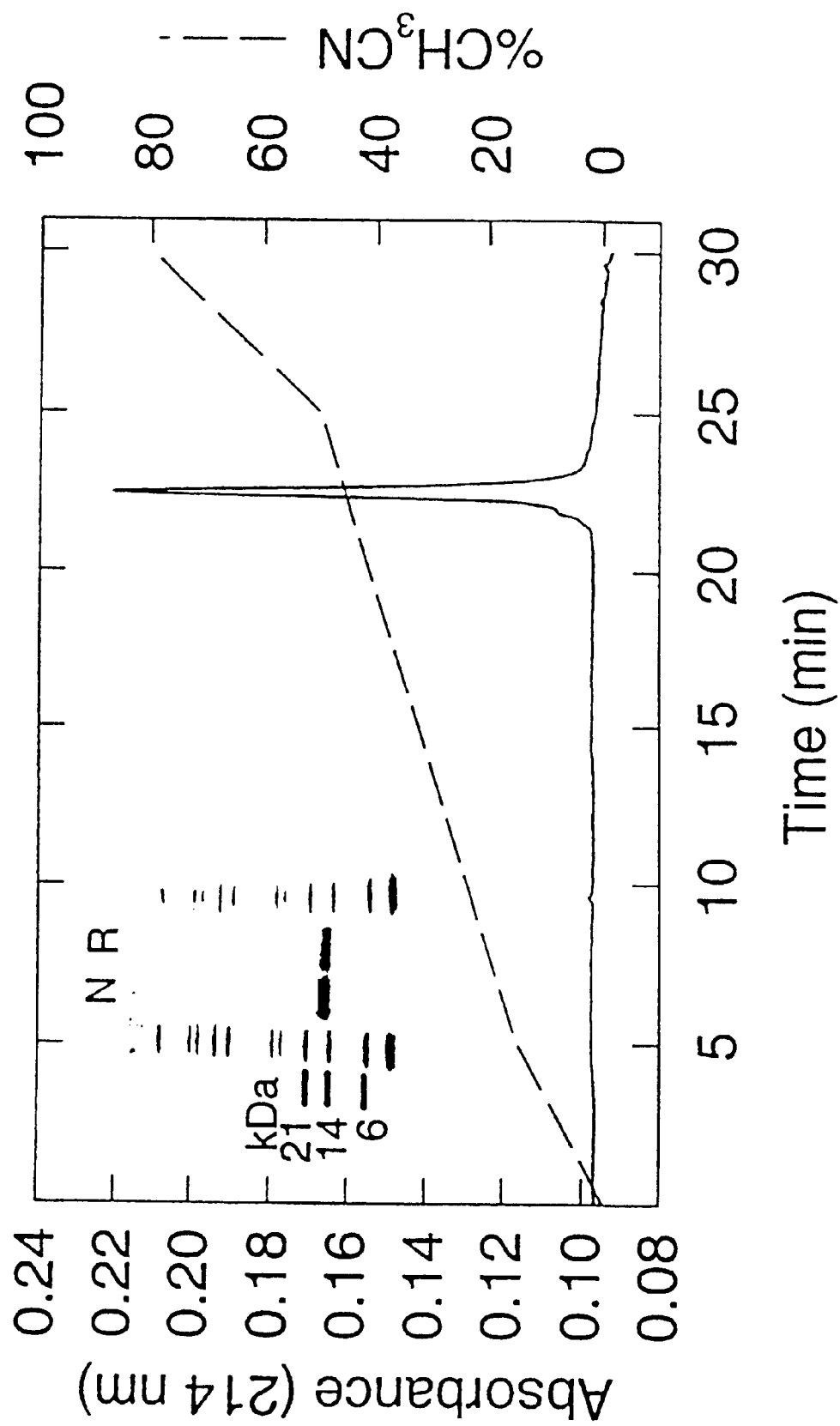
Figure 8A:
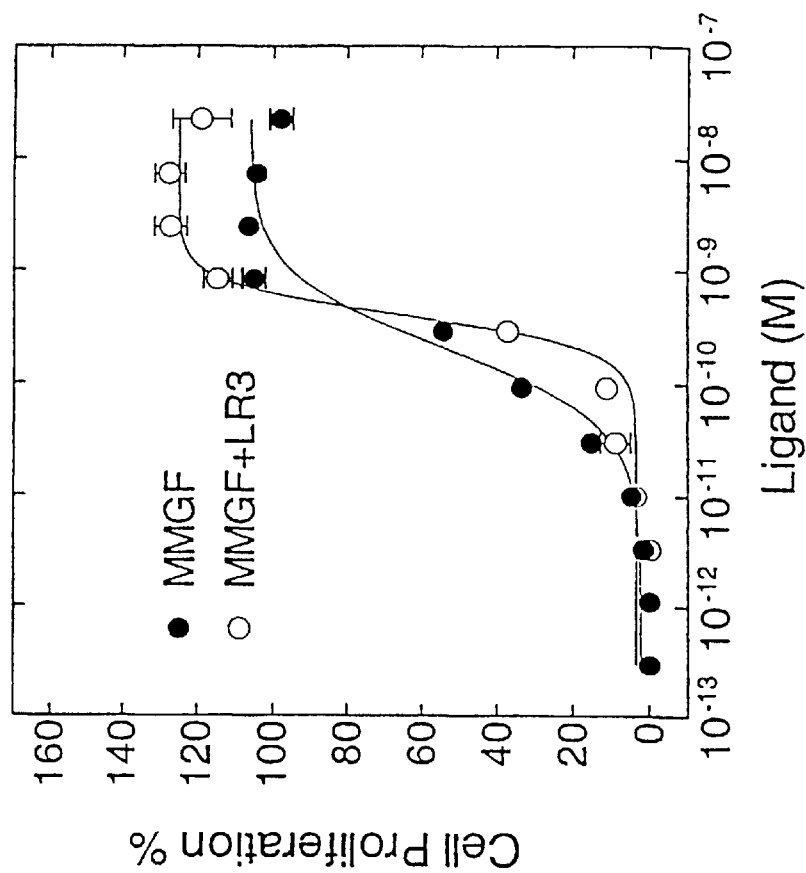
Figure 8B:
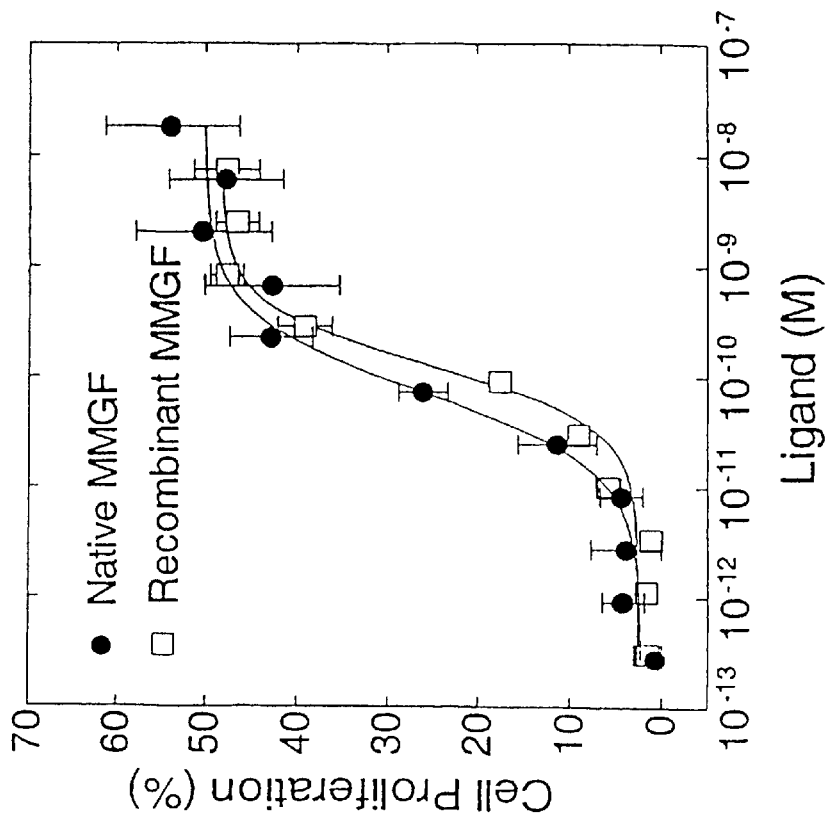
Figure 8D:
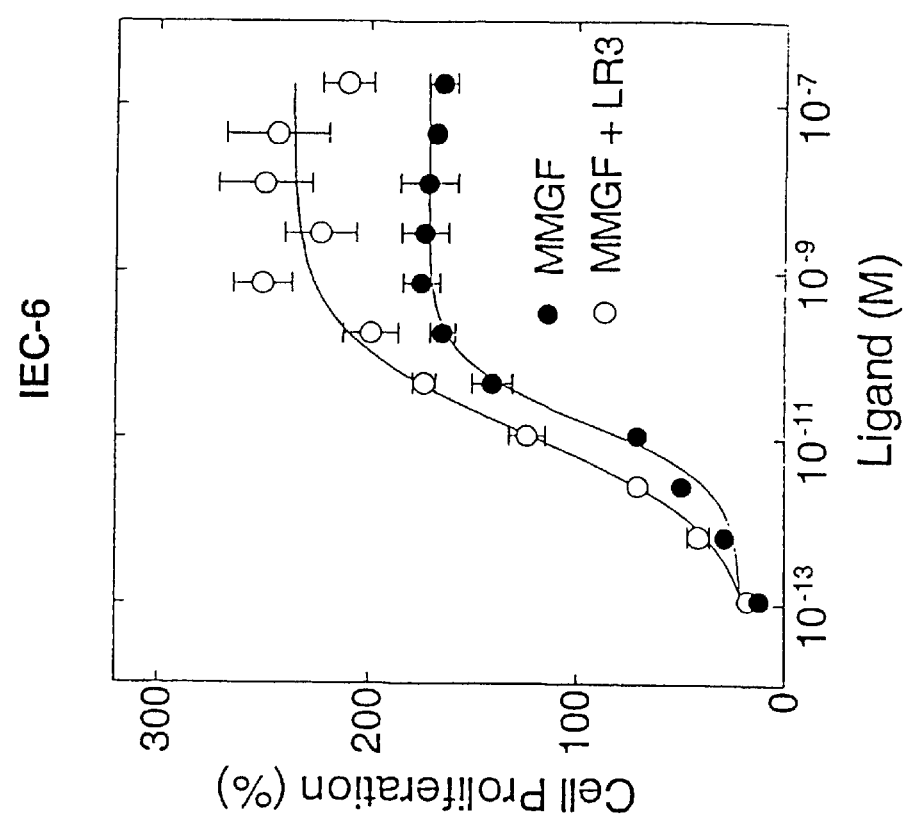
Figure 8C:
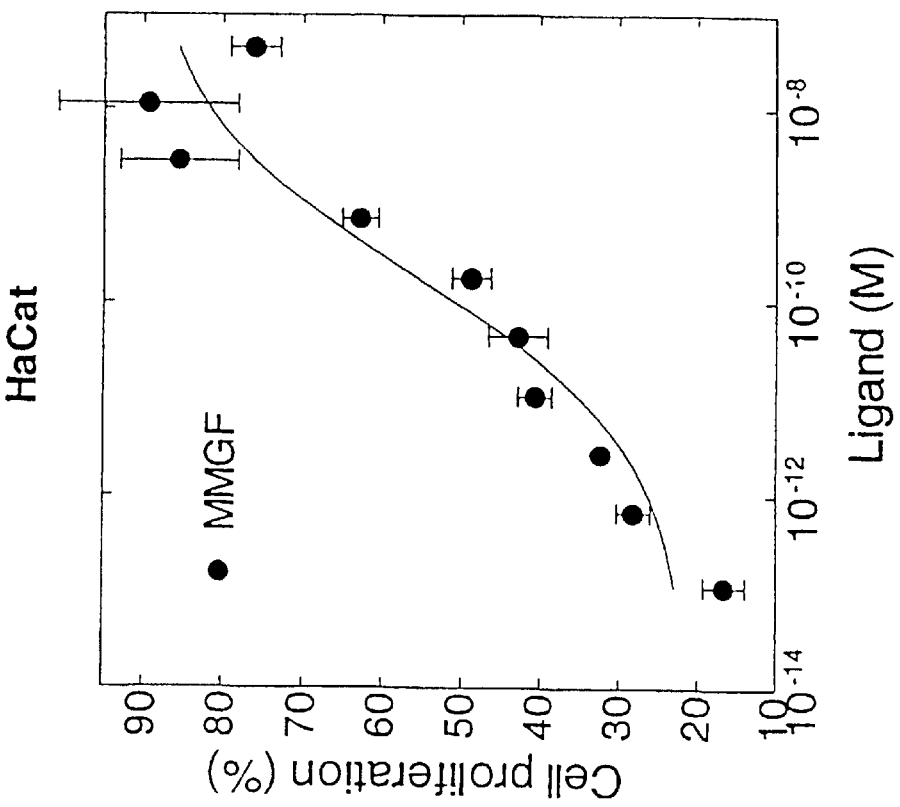
Figure 8F:
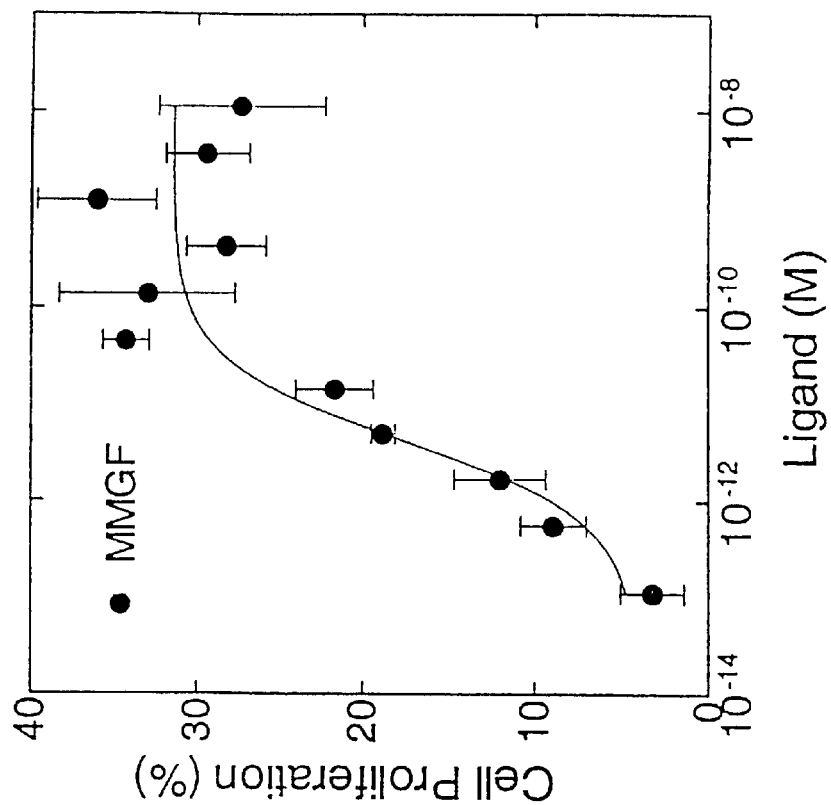
Figure 8E:
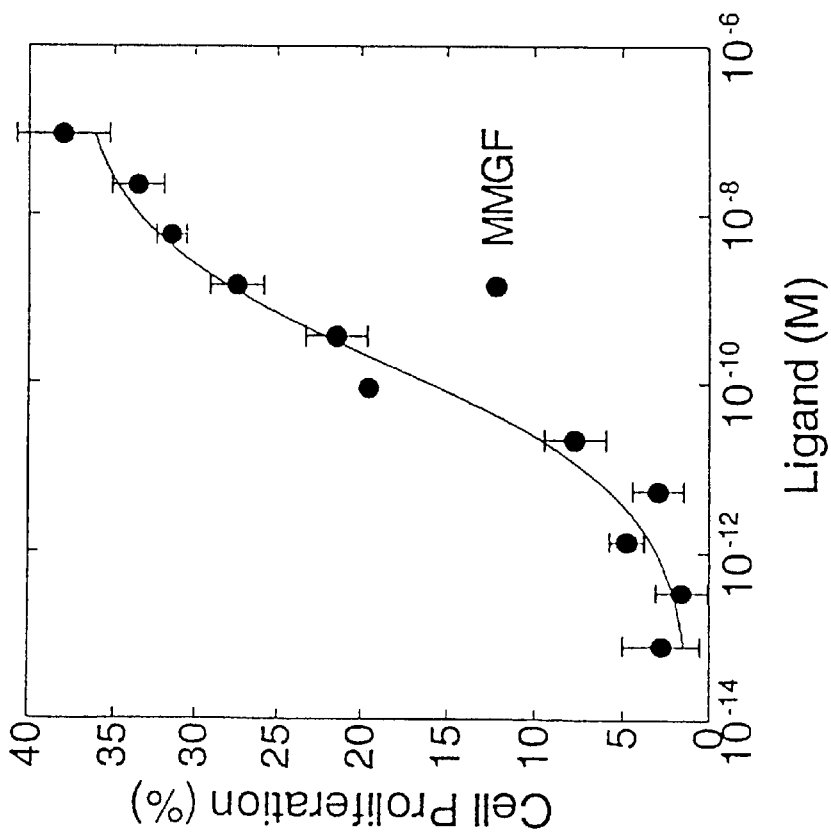
Figure 8G:
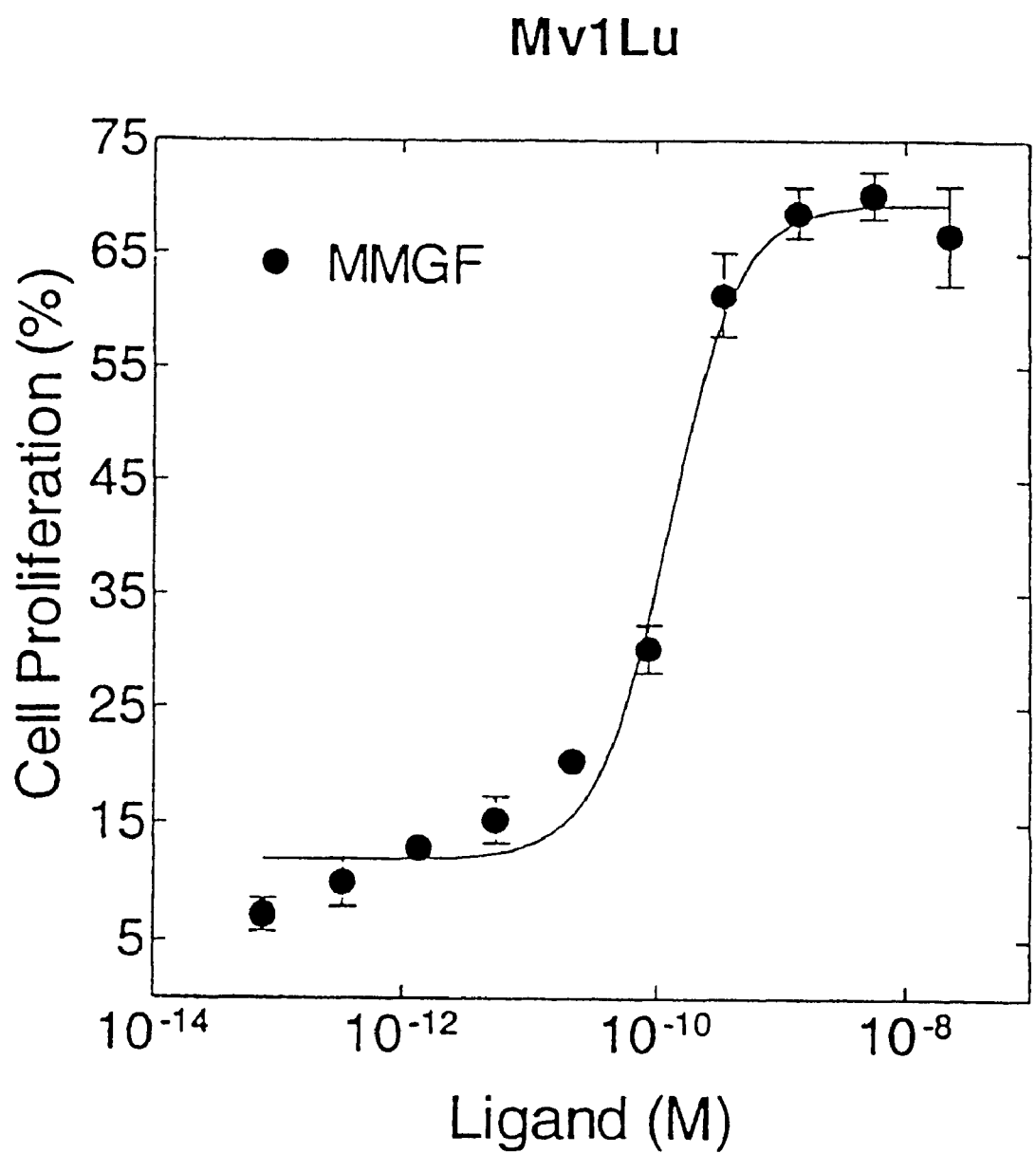

Analysis of the fusion protein pool by microbore C4 reverse-phase HPLC (2.1 mm×100 mm, Brownlee Lab, Santa Clara, Calif.) identified a single protein peak (FIG. 7B). The purity of the BMGF preparation was further confirmed by N-terminal sequence analysis which gave the expected N-terminal sequence for BMGF with an approximate purity of >99%. A single protein of the expected 14.5 kDa was also detected following SDS-PAGE under reducing or non-reducing conditions (FIG. 7B, inset).

To produce authentic BMGF the fusion protein was cleaved by solubilising the lyophilised protein in 0.13 M HCl containing a 100-fold molar excess of cyanogen bromide at a protein concentration of 10 mg.ml$^{-1}$. The cleavage reaction was performed at room temperature in the dark for 25 h. Following cleavage, cyanogen bromide was removed from the reaction by ion-exchange chromatography as described above, except that the protein was eluted from the column batchwise with 1 M NaCl.

Authentic BMGF was separated from its fusion partner by reverse phase HPLC. The S-Sepharose protein pool was diluted: 1:4 (v/v) with 0.1% TFA and applied to a C4 Prep-Pak column (25 mm×100 mm; 300 Å, 15 μm; Millipore-Waters, Lane Cove, New South Wales, Australia) at a flow rate of 50 ml.min$^{-1}$. The column was washed with 0.1% TFA until $OD_{280\ nm}$ returned to baseline and the column then eluted with a gradient of 16–32% (v/v) acetonitrile over 150 min in the presence of 0.08% TFA at a flow rate of 20 ml.min$^{-1}$. Fractions of 26 ml were collected and those containing pure BMGF pooled.

Analysis of the final BMGF protein pool by microbore C4 reverse-phase HPLC (2.1 mm×100 mm) identified a single protein peak (FIG. 7A). The purity of the BMGF preparation was further confirmed by N-terminal sequence analysis which gave the expected N-terminal sequence for BMGF with an approximate purity of >99%. The molecular mass of recombinant BMGF determined by electrospray ionization mass spectrometry was 8995.1±0.83. This is consistent with the theoretical mass of 8995.02 calculated from the BMGF amino acid sequence. Following SDS-PAGE a single protein peak of approximately 9 kDa was detected under reducing or non-reducing conditions (FIG. 7A, inset).

Example 7

Mitogenic Activity of BMGF

The mitogenic activity of authentic BMGF and recombinant BMGF on a range of cell lines was determined by methylene blue cell proliferation assay. Cell lines were sub-cultured in 96 well plates at a density of 10–20×10$^4$ cells.ml$^{-1}$ and incubated overnight at 37° C., 5% $CO_2$. Plates were then washed extensively with DMEM to remove any residual medium after which either native or recombinant BMGF was added at various concentrations (see FIG. 8). In some cell lines the effect of co-incubation of BMGF with 50 ng.ml$^{-1}$ LR$^3$IGF-1 was tested. After incubation for 48 h, the plates were washed twice with 0.15 M NaCl, the monolayers of cells fixed, and the cell mass quantified by addition of 1% methylene blue and measuring Absorbance at 600 nm. Both the BMGF isolated from bovine cheese whey extract and BMGF produced recombinantly were equipotent in Balb/c 3T3 cells. BMGF stimulated a wide range of cell lines covering both epithelial cells, fibroblastic cells and osteoblast cells. These include Balb/c 3T3, HaCaT, IEC-6, SF3169, Mv1Lu and CalOst cells. In some cases, for example in the gut epithelial cell line IEC-6, BMGF acted synergistically with LR$^3$IGF-1.

Example 8

Effect of BMGF on Gut Growth

Osmotic mini-pumps containing vehicle (0.1 M acetic acid) or BMGF (500 μg/kg/day) were implanted subcutaneously in the suprascapular region of male Sprague Dawley rats (8 animals per treatment group) and the rats kept in Tecniplast metabolism cages for 7 days in an environment maintained at 25° C. with a 12 h light/dark cycle. Animals had a continual access to water and a high carbohydrate diet.

After 7 days the rats were sacrificed by $CO_2$ overdose and total gut weight measured. Total gut weight per kilogram body weight was 25% higher after 7 days in rats treated with BMGF (FIG. 9).

Example 9

Cream (O/W-type)

| Ingredients: | % |
|---|---|
| Sorbitan monostearate | 2.0 |
| Polyoxyethylene sorbitanmonostearate | 3.0 |
| Cetyl alcohol | 5.0 |
| Light liquid paraffin | 8.0 |
| Isopropyl myristate | 2.0 |
| Active substance BMGF | $1.0–10^{-5}$ |
| Propylene glycol | 2.0 |
| Glycerin | 2.0 |
| Deionised water | 76 |
| Preservatives and other q.s. stabilisers | |

Heat the aqueous phase to 55–60° C., dissolve the active substance in it, and disperse the melted lipid phase in it by vigorous stirring. Cool to room 5 temperature and homogenise. In a similar manner a cream comprising 0.4, 4, or 20 $\mu g.ml^{-1}$, respectively, can be produced. Of this cream 100 $ul.cm^{-2}$ of wound is applied.

Example 10

Ointment (W/O-type)

| Ingredients: | % |
|---|---|
| Sorbitan trioleate | 5.0 |
| Wax, microcrystalline | 3.0 |
| Light liquid paraffin | 9.0 |
| Isopropyl myristate | 10.0 |
| Lanolin alcohols | 3.0 |
| Active substance BMGF | $1.0–10^{-5}$ |
| Propylene glycol | 2.0 |
| Glycerin | 2.0 |
| Magnesium sulphate, hydrous | 0.7 |
| Deionised water | 65.3 |
| Preservatives and other q.s. | |

Dissolve the active substance in the aqueous phase with gentle heating, and disperse the solution in the melted lipid phase. Cool to room temperature and 5 homogenise. In a similar manner an ointment 100 $\mu l.cm^{-2}$ of wound is applied.

Example 11

Mouthwash

| Ingredients: | % |
|---|---|
| Active substance BMGF | $1.0–10^{-3}$ |
| Polyethylene glycol(7)-glycerol cocoate | 2.0 |
| Deionised water | 13 |
| Glycerin (86%) | 18 |
| Peppermint oil | 10 |
| Ethanol | 55 |
| Preservatives and other q.s. | |

Dissolve the active substance in deionised water. Add and dissolve PEG(7)-glyceryl cocoate and glycerin n the solution. Dissolve peppermint oil in ethanol and mix the two solutions with stirring. The solution is to be diluted up to 1:10 before use.

Example 12

Parenteral Solution Ingredients

| | |
|---|---|
| Active substance BMGF | 1 $mg.ml^{-1}$ |
| ±Human Serum Albumin | 1 $mg.ml^{-1}$ |
| Arginine or Glycine | 20 $mg.ml^{-1}$ |
| ±Carbohydrate | 5–20 $mg.ml^{-1}$ |
| pH 7 | |

The carbohydrate is glucose, mannose, dextran, hydroxyethyl starch or a mixture thereof. The pH is adjusted with phosphate, succinate, amino acids or a mixture thereof.

Vials with 0.5 mg BMGF/0.5 ml are made and lyophilised.

| | |
|---|---|
| Active substance BMGF | $1.0–10^{-5}$ g |
| Methyl cellulose | 0.8 g |
| Calcium carbonate | 30 g |
| Colloidal silica | 3 g |
| Light liquid paraffin | 2 g |
| Glycerin | 20 g |
| Sweetening agent | |
| Flavouring agent | |
| Preservatives | |
| Deionised water to | 100 g |

The powders are wefted with the mixture of the active substance and methyl cellulose in a part of deionised water, paraffin and glycerin. The additives are added in solution. After making up with the remaining water the paste is homogenised.

Finally, it is to be understood that various alterations, modifications and/or additions may be made without departing from the spirit of the present invention as outlined herein.

What is claimed is:

1. An isolated polypeptide that is bovine milk growth factor (BMGF), comprising the following amino acid sequence:
DGNSTRSPEDDGLLCGDHAENC-PATTTQPKRRGHFSRCPKQYKHYCIKGR-CRFVVAEQTPSCVCDEGYAGARCERVDLFY (SEQ ID NO:2)
or an isolated polypeptide comprising a functionally active fragment thereof, that binds to an EGF receptor,
wherein said polypeptide is in a substantially purified or partially purified form.

2. The polypeptide of claim 1, wherein said polypeptide has a molecular weight of approximately 21–25 kDa as determined by SDS-PAGE.

3. The polypeptide of claim 1, wherein said polypeptide is in a non-glycosylated or partially non-glycosylated form and has a molecular weight of approximately 9–14 kDa as determined by SDS-PAGE.

4. The polypeptide of claim 1, wherein said polypeptide is obtained from bovine milk, milk products or milk product extracts.

5. A recombinant bovine milk growth factor (BMGF) encoded by an expression vector comprising a nucleic acid sequence encoding BMGF or a polypeptide comprising a functionally active fragment thereof,
wherein said nucleic acid sequence comprises SEQ ID NO:1 or a sequence coding for a polypeptide comprising a functionally active fragment thereof, that binds to an EGF receptor.

6. A recombinant fusion protein encoded by an expression vector comprising a nucleic acid sequence encoding bovine milk growth factor (BMGF) or a polypeptide comprising a functionally active fragment thereof,
wherein said nucleic acid sequence comprises SEQ ID NO:1 or a sequence coding for a polypeptide comprising a functionally active fragment that binds to an EGF receptor, and a nucleic acid sequence encoding a portion of porcine growth hormone (pGH) linked to the 5' nucleotide sequence of BMGF.

7. A method for isolating a substantially pure or partially pure polypeptide according to claim 1 from bovine milk, milk products, or, milk product extracts, comprising subjecting milk, milk products or milk product extracts to a chromatographic method or ultrafiltration method.

8. The method of claim 6, wherein said chromatographic method is selected from the group consisting of:
ion-exchange chromatography, size-exclusion chromatography, affinity chromatography and reverse-phase high performance liquid chromatography.

9. The method of claim 7, comprising the steps of:
providing bovine milk, milk product or milk product extract;
subjecting the bovine milk, milk product or milk product extract to ultrafiltration to obtain a first fraction;
subjecting the first fraction to anion exchange chromatography to obtain a second fraction;
subjecting the second fraction to gel filtration chromatography to obtain a third fraction;
subjecting the third fraction to reverse phase high performance liquid chromatography ((RP)HPLC) to obtain a fourth fraction;
subjecting the fourth fraction to affinity chromatography to obtain a fifth fraction;
subjecting the fifth fraction to (RP)HPLC to obtain a sixth fraction;
subjecting the sixth fraction to (RP)HPLC to obtain the substantially pure or partially pure bovine milk growth factor (BMGF).

10. The method of claim 7, further comprising a preliminary purification step wherein fats, solids and acidic proteins are removed from the milk, milk products or milk product extract prior to ultrafiltration.

11. The method of claim 7 further comprising the step of:
acidifying the milk, milk product or milk product extract, optionally to pH 2.5, prior to an ultrafiltration step.

12. The method of claim 9, wherein said ultrafiltration is performed using a membrane with an exclusion limit of approximately 50–150 kDa.

13. The method of claim 9, wherein the anion exchange chromatography is performed using an agarose-based anion exchange column.

14. The method of claim 9 wherein the gel filtration is performed using a column which separates proteins having molecular weights in the range of approximately 3 kDa to 70 kDa.

15. The method of claim 9 wherein the (RP)HPLC is performed using a C4 or C18 matrix.

16. The method of claim 9 wherein the affinity chromatography is performed using a heparin/agarose-based affinity column.

17. A composition of bovine milk growth factor (BMGF) purified from the first, second, third, fourth, fifth or sixth fraction according to the method of claim 9.

18. A composition comprising a polypeptide according to claim 1 and a carrier.

19. A recombinant fusion protein encoded by an expression vector comprising a nucleic acid sequence encoding BMGF or a polypeptide comprising a functionally active fragment thereof,
wherein said nucleic acid sequence comprises SEQ ID NO:1 or a sequence coding for a polypeptide comprising a functionally active fragment thereof, that binds to an EGF receptor, and
a nucleic acid sequence encoding a portion of porcine growth hormone (pGH) linked to the 5' nucleotide sequence of BMGF,
wherein the nucleic acid sequence encoding a portion of porcine growth hormone .(pGH) is linked. through a nucleic acid sequence encoding a cleavable amino acid sequence.

20. A method for promoting the growth and/or proliferation of mammalian cells and tissues, comprising the step of:
growing said cells or tissues in a culture medium including an effective amount of bovine milk growth factor (BMGF), fusion protein forms of BMGF according to claim 6 or 19, or a polypeptide comprising a functionally active fragment thereof, that binds to an EGF receptor, wherein said BMGF comprises SEQ ID NO:2.

21. A method for promoting the growth and/or proliferation of mammalian cells and tissues, comprising the step of:
growing said cells or tissues in a culture medium including an effective amount of bovine milk growth factor (BMGF), fusion protein forms of BMGF according to claim 6 or 19, or a polypeptide comprising a functionally active fragment thereof, that binds to an EGF receptor, together with an effective amount of an IGF, wherein said BMGF comprises SEQ ID NO:2.

22. The method of claim 21, wherein the IGF is the analogue LR$^3$ IGF-1.

23. A method for preventing, ameliorating or treating conditions associated with impaired gut function, comprising the step of:
   administering to a patient in need thereof an effective amount of bovine milk growth factor (BMGF), fusion protein forms of BMGF according to claim 6 or 19, or a polypeptide comprising a functionally active fragment of BMGF, that binds to an EGF receptor, wherein said BMGF comprises SEQ ID NO:2.

24. The isolated polypeptide according to claim 1, wherein said functionally active fragment is selected from the group consisting of SEQ ID NO:3, SEQ ID NO:4, SEQ ID NO:5, SEQ ID NO:6, SEQ ID NO:7, SEQ ID NO:8, and SEQ ID NO:9.

* * * * *

SEQUENCE LISTING

<160> NUMBER OF SEQ ID NOS: 21

<210> SEQ ID NO 1
<211> LENGTH: 240
<212> TYPE: DNA
<213> ORGANISM: Bos sp.
<220> FEATURE:
<221> NAME/KEY: CDS
<222> LOCATION: (1)..(240)

<400> SEQUENCE: 1

```
gat ggg aat tca acc aga agt cct gaa gat gat ggc ctt ctt tgt gga        48
Asp Gly Asn Ser Thr Arg Ser Pro Glu Asp Asp Gly Leu Leu Cys Gly
1               5                   10                  15 gat cac gca gaa aac tgc cca gct acc acc aca caa cca aag cga aga        96
Asp His Ala Glu Asn Cys Pro Ala Thr Thr Thr Gln Pro Lys Arg Arg
            20                  25                  30 ggc cac ttc tct cgg tgc ccc aag cag tac aag cat tac tgc att aaa       144
Gly His Phe Ser Arg Cys Pro Lys Gln Tyr Lys His Tyr Cys Ile Lys
        35                  40                  45 ggg aga tgt cgc ttc gtg gtg gcc gag cag acg ccc tcc tgc gtc tgt       192
Gly Arg Cys Arg Phe Val Val Ala Glu Gln Thr Pro Ser Cys Val Cys
    50                  55                  60 gat gaa ggc tat gct ggg gcc aga tgt gag aga gtt gac ttg ttt tac       240
Asp Glu Gly Tyr Ala Gly Ala Arg Cys Glu Arg Val Asp Leu Phe Tyr
65                  70                  75                  80
```

<210> SEQ ID NO 2
<211> LENGTH: 80
<212> TYPE: PRT
<213> ORGANISM: Bos sp.

<400> SEQUENCE: 2

```
Asp Gly Asn Ser Thr Arg Ser Pro Glu Asp Asp Gly Leu Leu Cys Gly
1               5                   10                  15

Asp His Ala Glu Asn Cys Pro Ala Thr Thr Thr Gln Pro Lys Arg Arg
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ala Gly Ala Arg Cys Glu Arg Val Asp Leu Phe Tyr
65                  70                  75                  80
```

<210> SEQ ID NO 3
<211> LENGTH: 35
<212> TYPE: PRT
<213> ORGANISM: Bos sp.

<400> SEQUENCE: 3

```
Asp Gly Asn Ser Thr Arg Ser Pro Glu Asp Asp Gly Leu Leu Cys Gly
1               5                   10                  15

Asp His Ala Glu Asn Cys Pro Ala Thr Thr Thr Gln Pro Lys Arg Arg
            20                  25                  30

Gly His Phe
        35
```

<210> SEQ ID NO 4
<211> LENGTH: 14
<212> TYPE: PRT

```
<213> ORGANISM: Bos sp.

<400> SEQUENCE: 4

Gly Tyr Ala Gly Ala Arg Cys Glu Arg Val Asp Leu Phe Tyr
1               5                   10

<210> SEQ ID NO 5
<211> LENGTH: 30
<212> TYPE: PRT
<213> ORGANISM: Bos sp.

<400> SEQUENCE: 5

Asp Gly Asn Ser Thr Arg Ser Pro Glu Asp Asp Gly Leu Leu Cys Gly
1               5                   10                  15

Asp His Ala Glu Asn Cys Pro Ala Thr Thr Thr Gln Pro Lys
            20                  25                  30

<210> SEQ ID NO 6
<211> LENGTH: 10
<212> TYPE: PRT
<213> ORGANISM: Bos sp.

<400> SEQUENCE: 6

Arg Arg Gly His Phe Ser Arg Cys Pro Lys
1               5                   10

<210> SEQ ID NO 7
<211> LENGTH: 3
<212> TYPE: PRT
<213> ORGANISM: Bos sp.

<400> SEQUENCE: 7

Gln Tyr Lys
1

<210> SEQ ID NO 8
<211> LENGTH: 5
<212> TYPE: PRT
<213> ORGANISM: Bos sp.

<400> SEQUENCE: 8

His Tyr Cys Ile Lys
1               5

<210> SEQ ID NO 9
<211> LENGTH: 32
<212> TYPE: PRT
<213> ORGANISM: Bos sp.

<400> SEQUENCE: 9

Gly Arg Cys Arg Phe Val Val Ala Glu Gln Thr Pro Ser Cys Val Cys
1               5                   10                  15

Asp Glu Gly Tyr Ala Gly Ala Arg Cys Glu Arg Val Asp Leu Phe Tyr
            20                  25                  30

<210> SEQ ID NO 10
<211> LENGTH: 33
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 10
```
atctaggtta ccatggatgg gaattcaacc aga                              33

<210> SEQ ID NO 11
<211> LENGTH: 33
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 11
atctaggtta ccggcgatgg gaattcaacc aga                              33

<210> SEQ ID NO 12
<211> LENGTH: 36
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 12
ctagataagc tttcatcagt aaaacaagtc aactct                           36

<210> SEQ ID NO 13
<211> LENGTH: 15
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 13
gggaattcaa ccaga                                                  15

<210> SEQ ID NO 14
<211> LENGTH: 18
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 14
gtaaaacaag tcaactct                                               18

<210> SEQ ID NO 15
<211> LENGTH: 24
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 15
gggaattcaa ccagaagtcc tgaa                                        24

<210> SEQ ID NO 16
<211> LENGTH: 27
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 16
gtaaaacaag tcaactctct cacacct                                     27

```
<210> SEQ ID NO 17
<211> LENGTH: 27
<212> TYPE: DNA
<213> ORGANISM: Artificial
<220> FEATURE:
<223> OTHER INFORMATION: Oligonucleotide Primer Obtained from Cell
      Sources that Produce Bovine Milk Growth Factor activity

<400> SEQUENCE: 17
gatgggaatt caaccagaag tcctgaa                                      27

<210> SEQ ID NO 18
<211> LENGTH: 35
<212> TYPE: PRT
<213> ORGANISM: Bos sp.
<220> FEATURE:
<221> NAME/KEY: UNSURE
<222> LOCATION: (1)..(35)
<223> OTHER INFORMATION: Xaa = any amino acid, unknown, or other

<400> SEQUENCE: 18

Asp Gly Xaa Ser Xaa Arg Ser Pro Glu Asp Asp Gly Leu Leu Cys Gly
1               5                   10                  15

Asp His Ala Glu Asn Cys Pro Ala Thr Thr Thr Gln Pro Lys Arg Arg
            20                  25                  30

Gly His Phe
        35

<210> SEQ ID NO 19
<211> LENGTH: 30
<212> TYPE: PRT
<213> ORGANISM: Bos sp.
<220> FEATURE:
<221> NAME/KEY: UNSURE
<222> LOCATION: (1)..(30)
<223> OTHER INFORMATION: Xaa = any amino acid, unknown, or other

<400> SEQUENCE: 19

Asp Gly Xaa Ser Xaa Arg Ser Pro Glu Asp Asp Gly Leu Leu Cys Gly
1               5                   10                  15

Asp His Ala Glu Asn Cys Pro Ala Thr Thr Thr Gln Pro Lys
            20                  25                  30

<210> SEQ ID NO 20
<211> LENGTH: 27
<212> TYPE: DNA
<213> ORGANISM: Bos sp.

<400> SEQUENCE: 20
tccatccagg ttaacatgga tgggaat                                      27

<210> SEQ ID NO 21
<211> LENGTH: 9
<212> TYPE: PRT
<213> ORGANISM: Bos sp.

<400> SEQUENCE: 21

Ser Ile Gln Val Asn Met Asp Gly Asn
1               5
```